US010946073B2

(12) United States Patent
Grinspoon

(10) Patent No.: US 10,946,073 B2
(45) Date of Patent: *Mar. 16, 2021

(54) GHRH OR ANALOGUES THEREOF FOR USE IN TREATMENT OF HEPATIC DISEASE

(71) Applicant: The General Hospital Corporation, Boston, MA (US)

(72) Inventor: Steven K. Grinspoon, Weston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/018,878

(22) Filed: Sep. 11, 2020

(65) Prior Publication Data

US 2020/0405816 A1 Dec. 31, 2020

Related U.S. Application Data

(63) Continuation of application No. 16/832,128, filed on Mar. 27, 2020, now Pat. No. 10,799,562.

(60) Provisional application No. 62/861,187, filed on Jun. 13, 2019, provisional application No. 62/826,284, filed on Mar. 29, 2016.

(51) Int. Cl.
  *A61K 38/25* (2006.01)
  *A61P 1/16* (2006.01)
  *A61K 9/00* (2006.01)

(52) U.S. Cl.
  CPC ............... *A61K 38/25* (2013.01); *A61P 1/16* (2018.01); *A61K 9/0019* (2013.01)

(58) Field of Classification Search
  CPC .......... A61K 38/25; A61K 9/0019; A61P 1/16
  See application file for complete search history.

(56) References Cited

U.S. PATENT DOCUMENTS

| 10,799,562 | B1 * | 10/2020 | Grinspoon | A61K 38/25 |
| 2008/0249017 | A1 | 10/2008 | Loughrey et al. | |
| 2015/0174207 | A1 | 6/2015 | Schally et al. | |
| 2016/0152735 | A1 | 6/2016 | Sabbadini et al. | |
| 2017/0296628 | A1 | 10/2017 | Peri | |
| 2019/0000854 | A1 | 1/2019 | Ilan et al. | |

OTHER PUBLICATIONS

Bedossa et al., "Biopsy and Noninvasive Methods to Assess Progression of Nonalcoholic Fatty Liver Disease", Gastroenterology: 2016, pp. 1811-1822, vol. 150.
Braun et al., "Effects of Pitavastatin on Insulin Sensitivity and Liver Fat: A Randomized Clinical Trial", The Journal of Clinical Endocrinology and Metabolism, 2018, pp. 4176-4186, vol. 103, No. 11, Endocrine Society.
Bredella et al., Breath-hold 1H-MR spectroscopy for intrahepatic lipid quantification at 3 Tesla, Author Manuscript of Journal of Computer Assisted Tomography, 2010, pp. 1-11, vol. 34, No. 3.
Chalasani et al., "The diagnosis and management of non-alcoholic fatty liver disease: practice guideline by the American Gastroenterological Association, American Association for the Study of Liver Diseases, and American College of Gastroenterology" Gastroenterology, 2012, pp. 1592-1609, vol. 142, No. 7, The AGA Institute, American College of Gastroenterology, and American Society for the Study of Liver Disease.
Cusi et al., "Long-Term Pioglitazone Treatment for Patients With Nonalcoholic Steatohepatitis and Prediabetes or Type 2 Diabetes Mellitus: A Randomized Trial", Annals of Internal Medicine, Sep. 6, 2016, pp. 305-315, vol. 165, No. 5, American College of Physicians.
Defronzo et al., "Glucose clamp technique: A method for quantifying insulin secretion and resistance", American Journal of Physiology, 1979, pp. E214-E223, vol. 273, No. 3.
Eckard et al., "Prospective histopathologic evaluation of lifestyle modification in nonalcoholic fatty liver disease: a randomized trial", Therapeutic Advances in Gastroenterology, 2013, pp. 249-259, vol. 6, No. 4, The Authors.
Ekstedt et al., "Fibrosis stage is the strongest predictor for disease-specific mortality in NAFLD after up to 33 years of follow-up" Hepatology, May 2015, pp. 1547-1554, vol. 61.
Erlandson et al., "Fat Matters: Understanding the Role of Adipose Tissue in Health in HIV Infection", Current HIV/AIDS Reports, 2016, pp. 20-30, vol. 13, Springer Science+Business Media New York.
Falutz et al., "Metabolic effects of a growth hormone-releasing factor in patients with HIV", The New England Journal of Medicine, Dec. 6, 2007, pp. 2359-2370, vol. 357, No. 23, Massachusetts Medical Society.
Falutz et al., "Effects of Tesamorelin (TH9507), a growth hormone-releasing factor analog, in human immunodeficiency virus-infected patients with excess abdominal fat: a pooled analysis of two multicenter, double-blind placebo-controlled phase 3 trials with safety extension data" Journal of Clinical Endocrinology & Metabolism, 2010, pp. 4291-4304, vol. 95, No. 9, The Endocrine Society.
Ferdinandi et al., "Non-Clinical Pharmacology and Safety Evaluation of TH9507, a Human Growth Hormone-Releasing Factor Analogue", Basic and Clincial Pharmacology and Toxicology, 2007, pp. 49-58, vol. 100.
Georgoff et al., "Hydrogen-1 MR spectroscopy for measurement and diagnosis of hepatic steatosis", American Journal of Roentgenology, 2012, pp. 2-7, vol. 199, American Roentgen Ray Society.
Ginès et al., "Screening for liver fibrosis in the general population: a call for action", The Lancet Gastroenterology & Hepatology, Nov. 2016, pp. 256-260, vol. 1.

(Continued)

*Primary Examiner* — Marcela M Cordero Garcia
(74) *Attorney, Agent, or Firm* — Foley & Lardner LLP

(57) ABSTRACT

The present application relates to novel methods for preventing, slowing the progression of, or treating nonalcoholic fatty liver (NAFL), nonalcoholic steatohepatitis (NASH), and/or liver fibrosis, and/or reducing the risks of liver cancer in subjects, such as HIV-infected subjects, using a GHRH molecule, e.g., trans-3-hexenoyl-GHRH$_{(1-44)}$-NH$_2$, or a pharmaceutically acceptable salt thereof. The subjects may have particular pathological features such as liver fibrosis, a hepatic fat fraction (HFF) of at least about 10%, serum alanine aminotransferase (ALT) levels of at least about 30 U/L, and/or a NAFLD Activity Score (NAS) of at least 4 or 5.

22 Claims, 5 Drawing Sheets

Specification includes a Sequence Listing.

(56) References Cited

OTHER PUBLICATIONS

Guaraldi et al., "Nonalcoholic fatty liver disease in HIV-Infected patients referred to a metabolic clinic: prevalence, characteristics, and predictors" Clinical Infectious Diseases, 2008, pp. 250-257, vol. 47, The Infectious Diseases Society of America.

Harris et al., "Research electronic data capture (REDCap)—A metadata-driven methodology and workflow process for providing translational research informatics support", Journal of Biomedical Informatics, 2009, pp. 377-381, vol. 42, Elsevier Inc.

Iogna Prat et al., "Etiology and Severity of Liver Disease in HIV-Positive Patients With Suspected NAFLD: Lessons From a Cohort With Available Liver Biopsies. Journal of Acquired Immune Deficiency Syndromes, Apr. 1, 2019, pp. 474-480, vol. 80, No. 4, Wolters Kluwer Health, Inc.

Kang et al., "Normal serum alanine aminotransferase and non-alcoholic fatty liver disease among Korean adolescents: a cross-sectional study using data from Knhanes 2010-2015", BMC Pediatrics, 2018, p. 215, vol. 18.

Katsagoni et al., "Effects of lifestyle interventions on clinical characteristics of patients with nonalcoholic fatty liver disease: A meta-analysis", Metabolism, 2017, pp. 119-132, vol. 68, Elsevier Inc.

Kim et al., "Comparative MR Study of Hepatic Fat Quantification Using Single-Voxel Proton Spectroscopy, Two-Point Dixon and Three-Point IDEAL", Magnetic Resonance in Medicine, Feb. 27, 2008, p. 521-527, vol. 59, No. 3, Wiley-Liss, Inc.

Kleiner et al., "Design and validation of a histological scoring system for nonalcoholic fatty liver disease" Hepatology, 2005, pp. 1313-1321, vol. 41, No. 6, The American Association for the Study of Liver Diseases.

Koutkia et al., "Growth Hormone (GH) Responses to GH-Releasing Hormone-Arginine Testing in Human Immunodeficiency Virus Lipodystrophy", The Journal of Endocrinology & Metabolism, Jan. 2005, pp. 32-38, vol. 90, No. 1, The Endocrine Society, USA.

Koutkia et al., "Growth Hormone-Releasing Hormone in HIV-Infected Men With Lipodystrophy: A Randomized Controlled Trial", JAMA, Jul. 14, 2004, pp. 210-218, vol. 292, No. 2, American Medical Association.

Kriska et al., "Development of questionnaire to examine relationship of physical activity and diabetes in Pima Indians", Diabetes Care, Apr. 1990, pp. 401-411, vol. 13, No. 4.

Lake et al., "Practical Review of Recognition and Management of Obesity and Lipohypertrophy in Human Immunodeficiency Virus Infection", Clinical Infectious Diseases, 2017, pp. 1-9, Oxford University Press for the Infectious Diseases Society of America.

Lavine et al., "Effect of Vitamin E or Metformin for Treatment of Nonalcoholic Fatty Liver Disease in Children and Adolescents: The TONIC Randomized Controlled Trial", JAMA, Apr. 27, 2011, pp. 1659-1668, vol. 305, No. 16, American Medical Association.

Makimura et al., "The effects of central adiposity on growth hormone (GH) response to GH-releasing hormone-arginine stimulation testing in men", The Journal of Endocrinology & Metabolism, 2008, pp. 4254-4260, vol. 93, No. 11, The Endocrine Society.

Maurice et al., "Prevalence and risk factors of nonalcoholic fatty liver disease in HIV-monoinfection", AIDS, 2017, pp. 1621-1632, vol. 31, No. 11, Wolters Kluwer Health, Inc.

Miller et al., "Meta-Analysis: high-dosage vitamin E supplementation may increase all-cause mortality", Annals of Internal Medicine, Jan. 4, 2005, pp. 37-47, vol. 142, No. 1, American College of Physicians.

Neuschwander-Tetri et al., "Farnesoid X nuclear receptor ligand obeticholic acid for non-cirrhotic, non-alcoholic steatohepatitis (FLINT): a multicentre, randomised, placebo-controlled trial", Lancet, Mar. 14, 2015, pp. 956-965, vol. 385.

Author Unknown, "Noncirrhotic Nonalcoholic Steatohepatitis With Liver Fibrosis: Developing Drugs for Treatment. Guidance for Industry", U.S. Department of Health and Human Services, Dec. 2018, (Accessed Mar. 17, 2019, 2019, at https://www.fda.gov/downloads/Drugs/GuidanceComplianceRegulatoryInformation/Guidances/UCM627376.pdf.).

Non-Final Office Action on U.S. Appl. No. 16/832,128 dated Jun. 22, 2020.

Notice of Allowance on U.S. Appl. No. 16/832,128 dated Aug. 28, 2020.

Nou et al., "Pathophysiology and management of cardiovascular disease in patients with HIV", Lancet Diabetes Endocrinology, Jul. 2016, pp. 598-610, vol. 4.

Author Unknown, Press Release. 2019. (Accessed Mar. 14, 2019, 2019, at http://ir.interceptpharma.com/news-releases/news-release-details/intercept-announces-positive-topline-results-pivotal-phase-3.).

Author Unknown, Press Release. Galmed Pharmaceuticals, 2018. (Accessed Mar. 14, 2019, 2019, at http://galmedpharma.investorroom.com/2018-02-14-Galmed-Announces-ARRIVE-Study-Data.).

Price et al., "Risk factors for fatty liver in the Multicenter AIDS Cohort Study", Author Manuscript of American Journal of Gastroenterology, May 2014, pp. 1-22, vol. 109, No. 5, The American College of Gastroenterology.

Rietschel et al., "Assessment of growth hormone dynamics in human immunodeficiency virus-related lipodystrophy", The Journal of Clinical Endocriniology & Metabolism, 2001, pp. 504-510, vol. 86, No. 2, The Endocrine Society.

Rockstroh, "Non-Alcoholic Fatty Liver Disease (NAFLD) and Non-Alcoholic Steatohepatitis (NASH) in HIV", Curr HIV/AIDS Rep, 2017, pp. 47-53, vol. 14, Springer Science+Business Media, New York 2017.

Rotman et al., "Current and upcoming pharmacotherapy for non-alcoholic fatty liver disease", Gut, Jan. 2017, pp. 180-190, vol. 66, Issue 1, London.

Sanyal et al., "Pioglitazone, Vitamin E, or Placebo for Nonalcoholic Steatohepatitis", The New England Journal of Medicine, 2010, pp. 1675-1685, vol. 362, No. 18, Massachusetts Medical Society.

Sato et al., "Vitamin E has a beneficial effect on nonalcoholic fatty liver disease: A meta-analysis of randomized controlled trials", Nutrition, 2015, pp. 923-930, vol. 31, Elsevier Inc.

Smith et al., "Trends in underlying causes of death in people with HIV from 1999 to 2011 (D:A:D): a multicohort collaboration" Lancet, Jul. 19, 2014, pp. 241-248, vol. 384.

Stanely et al., "Effect of Tesamorelin on Visceral Fat and Liver Fat in HIV-Infected Patients With Abdominal Fat Accumulation a Randomized Clinical Trial", the Journal of the American Medical Association, 2014, pp. 380-389, vol. 312, No. 4.

Stanley et al., "Effects of a Growth Hormone-Releasing Hormone Analog on Endogenous GH Pulsatility and Insulin Sensitivity in Healthy Men", Journal of Clinical Endocrinology & Metabolism, 2011, pp. 150-158, vol. 96, No. 1, The Endocrine Society.

Stanley et al., "Reduction in visceral adiposity is associated with an improved metabolic profile in HIV-infected patients receiving tesamorelin" Clinical Infectious Diseases, Jun. 1, 2012, pp. 1642-1651, vol. 54, Oxford University Press on behalf of the Infectious Diseases Society of America.

Stanley et al., "Growth Hormone Releasing Hormone Analogue Reduces Liver Fat in HIV-Infected Patients", Endocrine Society's 96$^{th}$ Annual Meeting and Expo, Jun. 21-24, 2014—Chicago, Presentation No. OR05-6, Date of Presentation: Jun. 21, 2014, 2 pages.

Sumida et al., "Current and future pharmacological therapies for NAFLD/NASH", Journal of Gastroenterology, 2018, pp. 362-376, vol. 53, Springer.

Tafesh et al., "Managing nonalcoholic fatty liver disease in patients living with HIV", Current Opinion Infectious Diseases, Feb. 2017, vol. 30, pp. 12-20, No. 1, Wolters Kluwer Health, Inc.

Grinspoon, "Tesamorelin Effects on Liver Fat and Histology in HIV", ClinicalTrials.gov, first posted Jul. 22, 2014.

Van Der Poorten et al., "Visceral Fat: a key mediator of steatohepatitis in metabolic liver disease", Hepatology, Aug. 2008, pp. 449-457, vol. 48, The American Association for the Study of Liver Diseases.

Vodkin et al., "Clinical, biochemical and histological differences between HIV-associated NAFLD and primary NAFLD: a case-control study", Alimentary Pharmacology and Therapuetics, 2015, pp. 368-378, vol. 41, John Wiley & Sons Ltd.

(56) References Cited

OTHER PUBLICATIONS

Wattacheril et al., "Nonalcoholic Steatohepatitis (NASH) and Hepatic Fibrosis: Emerging Therapies" Annual Review of Pharmacology and Toxicology, First published Oct. 20, 2017. pp. 649-662, vol. 58.

Yu et al., "Visceral Obesity Predicts Significant Fibrosis in Patients With Nonalcoholic Fatty Liver Disease", Medicine, Dec. 2015, pp. 1-7, vol. 94, No. 48, Wolters Kluwer Health, Inc.

Chalasani et al., "The Diagnosis and Management of Non-Alcoholic Fatty Liver Disease: Practice Guideline by the American Association for the Study of Liver Diseases, American College of Gastroenterology, and the American Gastroenterological Association", Hepatology, Jun. 2012, pp. 2005-2023, vol. 55, No. 6.

\* cited by examiner

| | Baseline | | | 12 month | | | |
|---|---|---|---|---|---|---|---|
| | Tesamorelin (n = 31) | Placebo (n = 30) | | Tesamorelin (n = 21) | Placebo (n = 26) | Treatment Effect* | P Value* |
| Liver Endpoints | | | | | | | |
| *Primary* | | | | | | | |
| Hepatic fat, absolute change, % | 12.9 ± 7.7 | 14.7 ± 9.0 | | 10.0 ± 7.9 | 14.5 ± 9.0 | -4.1 (-7.5, -0.7) | 0.02 |
| Hepatic fat, relative change, % | N/A | N/A | | -32 ± 54 | 5 ± 42 | -37 (-67, -7) | 0.02 |
| Resolution at 12 months, % | N/A | N/A | | 35 | 4 | 31 | 0.007 |
| *Secondary* | | | | | | | |
| ALT, U/L | 33 ± 25 | 26 ± 18 | | 26 ± 16 | 34 ± 29 | -7 (-15, 1) | 0.09 |
| GGT, U/L | 55 ± 54 | 65 ± 76 | | 45 ± 35 | 67 ± 86 | -19 (-43, 4) | 0.10 |
| Adipose tissue | | | | | | | |
| VAT, cm² | 232 ± 91 | 250 ± 104 | | 216 ± 108 | 257 ± 112 | -35 (-66, -4) | 0.03 |
| SAT, cm² | 290 ± 164 | 333 ± 156 | | 324 ± 187 | 352 ± 165 | 11 (-19, 41) | 0.46 |
| BMI, kg/m² | 30.1 ± 6.0 | 32.9 ± 6.2 | | 31.3 ± 7.3 | 33.5 ± 6.7 | 0.3 (-0.3, 0.9) | 0.37 |
| Waist, cm | 107 ± 15 | 114 ± 12 | | 109 ± 17 | 116 ± 14 | -1 (-5, 3) | 0.59 |
| Total body fat (kg) | 30.3 ± 10.5 | 34.4 ± 12.0 | | 32.5 ± 12.3 | 36.7 ± 12.5 | -0.7 (-3.3, 2.0) | 0.61 |
| Total lean body mass (kg)** | 57.2 ± 10.2 | 63.8 ± 10.6 | | 58.1 ± 10.7 | 63.9 ± 10.4 | 1.9 (-0.0, 3.8) | 0.05 |
| Metabolic Indices | | | | | | | |
| IGF-1, ng/mL | 132 ± 43 | 115 ± 43 | | 238 ± 87 | 116 ± 45 | 117 (76, 157) | < 0.0001 |
| Triglycerides, mg/dL | 151 ± 84 | 128 ± 46 | | 141 ± 70 | 126 ± 39 | 23 (-7, 53) | 0.12 |
| HDL-C, mg/dL | 47 ± 13 | 45 ± 11 | | 51 ± 12 | 44 ± 10 | 3 (-1, 6) | 0.17 |
| LDL-C, mg/dL | 113 ± 36 | 102 ± 25 | | 109 ± 37 | 105 ± 35 | -5 (-21, 11) | 0.54 |
| CRP, mg/L | 7.8 ± 9.9 | 4.2 ± 3.5 | | 5.8 ± 6.4 | 6.0 ± 5.6 | -4.7 (-9.2, -0.2) | 0.04 |
| Adiponectin, ng/mL | 2042 ± 1450 | 1638 ± 875 | | 2179 ± 1354 | 1233 ± 684 | 222 (-225, 669) | 0.32 |
| Glucose homeostasis | | | | | | | |
| Fasting glucose, mg/dL | 96 ± 20 | 97 ± 16 | | 98 ± 21 | 100 ± 14 | 4 (-5, 13) | 0.40 |
| HbA1c, % | 5.7 ± 0.5 | 5.8 ± 0.5 | | 5.9 ± 0.7 | 5.8 ± 0.6 | 0.2 (-0.1, 0.5) | 0.29 |
| CD4⁺ T-cells (cells/mm³) | 733 ± 290 | 798 ± 260 | | 731 ± 280 | 751 ± 270 | 17 (-60, 95) | 0.65 |
| CD8⁺ T-cells (cells/mm³) | 865 ± 380 | 967 ± 374 | | 775 ± 336 | 916 ± 378 | -18 (-113, 77) | 0.70 |
| log HIV viral load (copies/mL) | 0.34 ± 0.59 | 0.50 ± 0.74 | | 0.53 ± 0.80 | 0.49 ± 0.70 | 0.18 (-0.25, 0.62) | 0.41 |

FIG. 2

SEQUENCE LISTING

```
<160> NUMBER OF SEQ ID NOS: 4

<210> SEQ ID NO 1
<211> LENGTH: 44
<212> TYPE: PRT
<213> ORGANISM: Artificial sequence
<220> FEATURE:
<223> OTHER INFORMATION: Modified GRF peptide
<220> FEATURE:
<221> NAME/KEY: MISC_FEATURE
<222> LOCATION: (1)..(1)
<223> OTHER INFORMATION: Tyr residue is linked to an hexenoyl-trans-3
      moiety
<220> FEATURE:
<221> NAME/KEY: MOD_RES
<222> LOCATION: (44)..(44)
<223> OTHER INFORMATION: AMIDATION

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 2
<211> LENGTH: 44
<212> TYPE: PRT
<213> ORGANISM: Artificial sequence
```

```
<220> FEATURE:
<223> OTHER INFORMATION: GRF peptide
<220> FEATURE:
<221> NAME/KEY: VARIANT
<222> LOCATION: (1)..(1)
<223> OTHER INFORMATION: Xaa = Tyr or His
<220> FEATURE:
<221> NAME/KEY: VARIANT
<222> LOCATION: (2)..(2)
<223> OTHER INFORMATION: Xaa = Val or Ala
<220> FEATURE:
<221> NAME/KEY: VARIANT
<222> LOCATION: (8)..(8)
<223> OTHER INFORMATION: Xaa = Asn or Ser
<220> FEATURE:
<221> NAME/KEY: VARIANT
<222> LOCATION: (13)..(13)
<223> OTHER INFORMATION: Xaa = Val or Ile
<220> FEATURE:
<221> NAME/KEY: VARIANT
<222> LOCATION: (15)..(15)
<223> OTHER INFORMATION: Xaa = Ala or Gly
<220> FEATURE:
<221> NAME/KEY: VARIANT
<222> LOCATION: (18)..(18)
<223> OTHER INFORMATION: Xaa = Ser or Tyr
<220> FEATURE:
<221> NAME/KEY: VARIANT
<222> LOCATION: (24)..(24)
<223> OTHER INFORMATION: Xaa = Gln or His
<220> FEATURE:
<221> NAME/KEY: VARIANT
<222> LOCATION: (25)..(25)
<223> OTHER INFORMATION: Xaa = Asp or Glu
<220> FEATURE:
<221> NAME/KEY: VARIANT
<222> LOCATION: (27)..(27)
<223> OTHER INFORMATION: Xaa = Met or Ile or Nle
<220> FEATURE:
<221> NAME/KEY: VARIANT
<222> LOCATION: (28)..(28)
<223> OTHER INFORMATION: Xaa = Ser or Asn
<220> FEATURE:
<221> NAME/KEY: VARIANT
<222> LOCATION: (30)..(30)
<223> OTHER INFORMATION: Xaa = any amino acid or is absent
<220> FEATURE:
<221> NAME/KEY: VARIANT
<222> LOCATION: (31)..(31)
<223> OTHER INFORMATION: Xaa = any amino acid or is absent
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: VARIANT
<222> LOCATION: (33)..(33)
<223> OTHER INFORMATION: Xaa = any amino acid or is absent
<220> FEATURE:
<221> NAME/KEY: VARIANT
<222> LOCATION: (34)..(34)
<223> OTHER INFORMATION: Xaa = any amino acid or is absent
<220> FEATURE:
<221> NAME/KEY: VARIANT
<222> LOCATION: (35)..(35)
<223> OTHER INFORMATION: Xaa = any amino acid or is absent
<220> FEATURE:
<221> NAME/KEY: VARIANT
<222> LOCATION: (36)..(36)
<223> OTHER INFORMATION: Xaa = any amino acid or is absent
<220> FEATURE:
<221> NAME/KEY: VARIANT
<222> LOCATION: (37)..(37)
<223> OTHER INFORMATION: Xaa = any amino acid or is absent
<220> FEATURE:
<221> NAME/KEY: VARIANT
<222> LOCATION: (38)..(38)
<223> OTHER INFORMATION: Xaa = any amino acid or is absent
<220> FEATURE:
```

```
<221> NAME/KEY: VARIANT
<222> LOCATION: (39)..(39)
<223> OTHER INFORMATION: Xaa = any amino acid or is absent
<220> FEATURE:
<221> NAME/KEY: VARIANT
<222> LOCATION: (40)..(40)
<223> OTHER INFORMATION: Xaa = any amino acid or is absent
<220> FEATURE:
<221> NAME/KEY: VARIANT
<222> LOCATION: (41)..(41)
<223> OTHER INFORMATION: Xaa = any amino acid or is absent
<220> FEATURE:
<221> NAME/KEY: VARIANT
<222> LOCATION: (42)..(42)
<223> OTHER INFORMATION: Xaa = any amino acid or is absent
<220> FEATURE:
<221> NAME/KEY: VARIANT
<222> LOCATION: (43)..(43)
<223> OTHER INFORMATION: Xaa = any amino acid or is absent
<220> FEATURE:
<221> NAME/KEY: VARIANT
<222> LOCATION: (44)..(44)
<223> OTHER INFORMATION: Xaa = any amino acid or is absent

<400> SEQUENCE: 2

Xaa Xaa Asp Ala Ile Phe Tyr Xaa Ser Tyr Arg Lys Xaa Leu Xaa Gln
1               5                   10                  15

Leu Xaa Ala Arg Lys Leu Leu Xaa Xaa Ile Xaa Xaa Arg Xaa Xaa Xaa
            20                  25                  30

Xaa Xaa Xaa Xaa Xaa Xaa Xaa Xaa Xaa Xaa Xaa Xaa
        35                  40

<210> SEQ ID NO 3
<211> LENGTH: 15
<212> TYPE: PRT
<213> ORGANISM: Artificial sequence
<220> FEATURE:
<223> OTHER INFORMATION: Amino acid sequence corresponding to positions
      30 to 44 of the human GRF

<400> SEQUENCE: 3

Gln Gln Gly Glu Ser Asn Gln Glu Arg Gly Ala Arg Ala Arg Leu
1               5                   10                  15

<210> SEQ ID NO 4
<211> LENGTH: 44
<212> TYPE: PRT
<213> ORGANISM: Homo sapiens

<400> SEQUENCE: 4

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40
```

GHRH OR ANALOGUES THEREOF FOR USE IN TREATMENT OF HEPATIC DISEASE

CROSS REFERENCE TO RELATED APPLICATIONS

The present application is a continuation of U.S. patent application Ser. No. 16/832,128, filed on Mar. 27, 2020, which claims the benefit of U.S. Provisional application No. 62/826,284, filed on Mar. 29, 2019, and of U.S. Provisional application No. 62/861,187, filed on Jun. 13, 2019, which are incorporated herein by reference.

STATEMENT REGARDING FEDERALLY SPONSORED RESEARCH OR DEVELOPMENT

This invention was made with Government support under National Institutes of Health, National Institute of Allergy and Infectious Diseases Grant No. U01 AI115711. The Government has certain rights in this invention.

SEQUENCE LISTING

This application contains a Sequence Listing in computer readable form entitled "11718_361_SeqList.txt", created on Mar. 25, 2020 and having a size of about 5 KB. The computer readable form is incorporated herein by reference.

TECHNICAL FIELD

The present disclosure generally relates to the management of liver disease, such as nonalcoholic fatty liver (NAFL), nonalcoholic steatohepatitis (NASH), and liver fibrosis.

BACKGROUND ART

NAFL is defined by excess storage of triglyceride in hepatocytes (steatosis) and is often characterized by resultant inflammation, cellular ballooning and damage, and fibrosis. Significant changes in this regard lead to NASH. Nonalcoholic fatty liver disease (NAFLD) may progress to fibrosis and ultimately cirrhosis and is an increasingly important cause of end-stage liver disease in the general population, and has also been studied in people living with HIV (PLWH; Rockstroh J K. *Curr HIV/AIDS Rep* 2017; 14:47-53; Vodkin I, et al. *Aliment Pharmacol Ther* 2015; 41:368-78). NAFL/NASH have a higher prevalence in HIV patients and tend to progress faster than in the general population. In contrast to many HIV-associated comorbidities that worsen with increased HIV-disease severity, NAFLD may occur more commonly in HIV patients with higher $CD4^+$ T-cell counts and weight gain and it is associated with central adiposity (Guaraldi G, et al. Clin Infect Dis 2008; 47:250-7; van der Poorten D, et al. Hepatology 2008; 48:449-57; Maurice J B, et al. AIDS 2017; 31:1621-32). In PLWH, weight gain, abdominal fat accumulation, and increases in visceral fat are common and seen even with newer antiretrovirals (Lake J E, et al. Clin Infect Dis 2017; 64:1422-9). Although Vitamin E (Sanyal A J. *N Engl J Med* 2010; 362:1675-85; Lavine J E, et al. *JAMA* 2011; 305: 1659-68; Sato K, et al. *Nutrition* 2015; 31:923-30) and pioglitazone[7] have been shown to improve histological features of NASH in the general population, there are no proven pharmacologic therapies for NAFLD or NASH in people living with HIV. One product, aramchol (an oral stearoyl-coenzyme-A-desaturase-1 inhibitor known to reduce hepatic-fat content in patients with primary NAFLD), was assessed in patients with HIV-associated NAFLD and it had no significant effect in this specific patient population (Ajmera et al., Hepatology. 2019 Apr. 23. doi: 10.1002/hep.30674. [Epub ahead of print]).

Liver fibrosis results from chronic damage to the liver in conjunction with the accumulation of extracellular matrix (ECM) proteins, which is a characteristic of most types of chronic liver diseases. Advanced liver fibrosis results in cirrhosis, liver failure, and portal hypertension and often requires liver transplantation. There is currently no effective therapy that effectively target liver fibrosis associated with NAFL/NASH.

There is thus a need for novel therapies for the management of NAFLD, NASH and/or liver fibrosis, notably in HIV-infected patients.

The present description refers to a number of documents, the content of which is herein incorporated by reference in their entirety.

SUMMARY OF THE DISCLOSURE

The present disclosure generally relates to the management of liver disease, such as nonalcoholic fatty liver disease (NAFLD). NAFLD refers to a fatty liver that is not related to alcohol use, and is further divided into nonalcoholic fatty liver (NAFL) and nonalcoholic steatohepatitis (NASH) with or without fibrosis, and in an aspect relates to the use of growth hormones (GH) secretagogues, and more specifically to Growth Hormone-Releasing Hormone (GHRH) or analogs thereof for use in the management (including prevention and/or treatment) of such liver disease or related conditions.

In various aspects and embodiments, the present disclosure provides the following items:

1. A method for preventing or treating nonalcoholic fatty liver (NAFL) or nonalcoholic steatohepatitis (NASH) in a subject in need thereof comprising administering an effective amount of trans-3-hexenoyl-$GHRH_{(1-44)}$-$NH_2$ or a pharmaceutically acceptable salt thereof to said subject, wherein said subject has (i) a hepatic fat fraction (HFF) of at least about 5% or 10% as measured by proton magnetic resonance spectroscopy ($^1$H MRS) (or any other suitable method; (ii) serum alanine aminotransferase (ALT) levels of at least about 25 or 30 U/L; (iii) a NAFLD Activity Score (NAS) of at least 3, 4 or 5 as measured by the NAS Clinical Research Network (NAS CRN) scoring system; (iv) liver fibrosis or (iv) any combination of (i) to (iv).
2. The method of item 1, wherein said subject has an HFF of at least about 5% or 10%.
3. The method of item 1, wherein said subject has an HFF of at least about 15%.
4. The method of item 1, wherein said subject has an HFF of at least about 20%.
5. The method of any one of items 1 to 4, wherein said subject has serum ALT levels of at least about 25 or 30 U/L.
6. The method of any one of items 1 to 4, wherein said subject has serum ALT levels of at least about 35 U/L.
7. The method of any one of items 1 to 6, wherein said subject has a NAS of at least 6.
8. The method of item 7, wherein said subject has a NAS of at least 7.
9. The method of any one of items 1 to 8, wherein said subject has liver fibrosis, for example stage 1A liver fibrosis or worse, preferably stage 1C or stage 2 liver fibrosis or worse.

10. The method of any one of items 1 to 9, wherein said subject suffers from human immunodeficiency virus (HIV) infection.

11. The method of any one of items 1 to 10, wherein said subject has a body mass index (BMI) of at least about 25.

12. The method of item 11, wherein said subject has a BMI of at least about 30.

13. The method of any one of items 1 to 12, wherein said method comprises administering an effective amount of a pharmaceutically acceptable salt of trans-3-hexenoyl-GHRH$_{(1-44)}$-NH$_2$ to said subject.

14. The method of item 13, wherein said pharmaceutically acceptable salt of trans-3-hexenoyl-GHRH$_{(1-44)}$-NH$_2$ is an acetate salt.

15. The method of any one of items 1 to 14, wherein said trans-3-hexenoyl-GHRH$_{(1-44)}$-NH$_2$ or pharmaceutically acceptable salt thereof is administered at a daily dose of about 1 mg to about 4 mg.

16. The method of item 15, wherein said trans-3-hexenoyl-GHRH$_{(1-44)}$-NH$_2$ or pharmaceutically acceptable salt thereof is administered at a daily dose of about 1 mg to about 2 mg.

17. The method of any one of items 1 to 16, wherein said trans-3-hexenoyl-GHRH$_{(1-44)}$-NH$_2$ or pharmaceutically acceptable salt thereof is administered by subcutaneous injection.

18. The method of any one of items 1 to 17, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

19. The method of item 18, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

20. The method of item 18, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

21. Trans-3-hexenoyl-GHRH$_{(1-44)}$-NH$_2$ or a pharmaceutically acceptable salt thereof for use in the prevention or treatment of nonalcoholic fatty liver (NAFL) or nonalcoholic steatohepatitis (NASH) in a subject, wherein said subject has (i) a hepatic fat fraction (HFF) of at least about 5 or 10% as measured by proton magnetic resonance spectroscopy ($^1$H MRS); (ii) serum alanine aminotransferase (ALT) levels of at least about 25 or 30 U/L; (iii) a NAFLD Activity Score (NAS) of at least 5 as measured by the NAS Clinical Research Network (NAS CRN) scoring system; or (iv) any combination of (i) to (iii).

22. The trans-3-hexenoyl-GHRH$_{(1-44)}$-NH$_2$ or pharmaceutically acceptable salt thereof for use according to item 21, wherein said subject has an HFF of at least about 5 or 10%.

23. The trans-3-hexenoyl-GHRH$_{(1-44)}$-NH$_2$ or pharmaceutically acceptable salt thereof for use according to item 21, wherein said subject has an HFF of at least about 15%.

24. The trans-3-hexenoyl-GHRH$_{(1-44)}$-NH$_2$ or pharmaceutically acceptable salt thereof for use according to item 21, wherein said subject has an HFF of at least about 20%.

25. The trans-3-hexenoyl-GHRH$_{(1-44)}$-NH$_2$ or pharmaceutically acceptable salt thereof for use according to any one of items 21 to 24, wherein said subject has serum ALT levels of at least about 25 or 30 U/L.

26. The trans-3-hexenoyl-GHRH$_{(1-44)}$-NH$_2$ or pharmaceutically acceptable salt thereof for use according to any one of items 21 to 24, wherein said subject has serum ALT levels of at least about 35 U/L.

27. The trans-3-hexenoyl-GHRH$_{(1-44)}$-NH$_2$ or pharmaceutically acceptable salt thereof for use according to any one of items 21 to 26, wherein said subject has a NAS of at least 6.

28. The trans-3-hexenoyl-GHRH$_{(1-44)}$-NH$_2$ or pharmaceutically acceptable salt thereof for use according to item 27, wherein said subject has a NAS of at least 7.

29. The trans-3-hexenoyl-GHRH$_{(1-44)}$-NH$_2$ or pharmaceutically acceptable salt thereof for use according to any one of items 21 to 28, wherein said subject has liver fibrosis, for example stage 1A liver fibrosis or worse, preferably stage 1C or stage 2 liver fibrosis or worse.

30. The trans-3-hexenoyl-GHRH$_{(1-44)}$-NH$_2$ or pharmaceutically acceptable salt thereof for use according to any one of items 21 to 29, wherein said subject suffers from human immunodeficiency (HIV) infection.

31. The trans-3-hexenoyl-GHRH$_{(1-44)}$-NH$_2$ or pharmaceutically acceptable salt thereof for use according to any one of items 21 to 31, wherein said subject has a body mass index (BMI) of at least about 25.

32. The trans-3-hexenoyl-GHRH$_{(1-44)}$-NH$_2$ or pharmaceutically acceptable salt thereof for use according to item 31, wherein said subject has a BMI of at least about 30.

33. The trans-3-hexenoyl-GHRH$_{(1-44)}$-NH$_2$ or pharmaceutically acceptable salt thereof for use according to any one of items 21 to 33, wherein a pharmaceutically acceptable salt of trans-3-hexenoyl-GHRH$_{(1-44)}$-NH$_2$ is used.

34. The trans-3-hexenoyl-GHRH$_{(1-44)}$-NH$_2$ or pharmaceutically acceptable salt thereof for use according to item 33, wherein said pharmaceutically acceptable salt of trans-3-hexenoyl-GHRH$_{(1-44)}$-NH$_2$ is an acetate salt.

35. The trans-3-hexenoyl-GHRH$_{(1-44)}$-NH$_2$ or pharmaceutically acceptable salt thereof for use according to any one of items 21 to 34, wherein said trans-3-hexenoyl-GHRH$_{(1-44)}$-NH$_2$ or pharmaceutically acceptable salt thereof is for administration at a daily dose of about 1 mg to about 4 mg.

36. The trans-3-hexenoyl-GHRH$_{(1-44)}$-NH$_2$ or pharmaceutically acceptable salt thereof for use according to item 37, wherein said trans-3-hexenoyl-GHRH$_{(1-44)}$-NH$_2$ or pharmaceutically acceptable salt thereof is for administration at a daily dose of about 1 mg to about 2 mg.

37. The trans-3-hexenoyl-GHRH$_{(1-44)}$-NH$_2$ or pharmaceutically acceptable salt thereof for use according to any one of items 21 to 36, wherein said trans-3-hexenoyl-GHRH$_{(1-44)}$-NH$_2$ or pharmaceutically acceptable salt thereof is for administration by subcutaneous injection.

38. The trans-3-hexenoyl-GHRH$_{(1-44)}$-NH$_2$ or pharmaceutically acceptable salt thereof for use according to any one of items 21 to 37, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

39. The trans-3-hexenoyl-GHRH$_{(1-44)}$-NH$_2$ or pharmaceutically acceptable salt thereof for use according to item 38, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

40. The trans-3-hexenoyl-GHRH$_{(1-44)}$-NH$_2$ or pharmaceutically acceptable salt thereof for use according to item 38, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

41. A method for (i) preventing or reducing the development or progression of liver fibrosis or (ii) reducing liver fibrosis in a subject, comprising administering an effective amount of trans-3-hexenoyl-GHRH$_{(1-44)}$-NH$_2$ or a pharmaceutically acceptable salt thereof to said subject.

42. The method of item 41, wherein said subject has a fibrosis score of at least 10 prior to the treatment.
43. The method of item 41, wherein said subject has a fibrosis score of at least 2 prior to the treatment.
44. The method of any one of items 41 to 43, wherein said subject has an HFF of at least about 10%.
45. The method of item 44, wherein said subject has an HFF of at least about 15%.
46. The method of item 45, wherein said subject has an HFF of at least about 20%.
47. The method of any one of items 41 to 46, wherein said subject has serum ALT levels of at least about 30 U/L.
48. The method of any one of items 41 to 46, wherein said subject has serum ALT levels of at least about 35 U/L.
49. The method of any one of items 41 to 48, wherein said subject has a NAFLD Activity Score (NAS) of at least 2 as measured by the NAS Clinical Research Network (NAS CRN) scoring system.
50. The method of item 49, wherein said subject has a NAS of at least 3.
51. The method of any one of items 41 to 50, wherein said subject suffers from human immunodeficiency virus (HIV) infection.
52. The method of any one of items 41 to 51, wherein said subject has a body mass index (BMI) of at least about 25.
53. The method of item 52, wherein said subject has a BMI of at least about 30.
54. The method of any one of items 41 to 53, wherein said method comprises administering an effective amount of a pharmaceutically acceptable salt of trans-3-hexenoyl-GHRH$_{(1-44)}$-NH$_2$ to said subject.
55. The method of item 54, wherein said pharmaceutically acceptable salt of trans-3-hexenoyl-GHRH$_{(1-44)}$-NH$_2$ is an acetate salt.
56. The method of any one of items 41 to 55, wherein said trans-3-hexenoyl-GHRH$_{(1-44)}$-NH$_2$ or pharmaceutically acceptable salt thereof is administered at a daily dose of about 1 mg to about 4 mg.
57. The method of item 56, wherein said trans-3-hexenoyl-GHRH$_{(1-44)}$-NH$_2$ or pharmaceutically acceptable salt thereof is administered at a daily dose of about 1 mg to about 2 mg.
58. The method of any one of items 41 to 57, wherein said trans-3-hexenoyl-GHRH$_{(1-44)}$-NH$_2$ or pharmaceutically acceptable salt thereof is administered by subcutaneous injection.
59. The method of any one of items 41 to 58, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.
60. The method of item 59, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.
61. The method of item 59, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.
62. Trans-3-hexenoyl-GHRH$_{(1-44)}$-NH$_2$ or a pharmaceutically acceptable salt thereof for use in (i) preventing or reducing the development or progression of liver fibrosis or (ii) reducing liver fibrosis in a subject.
63. The trans-3-hexenoyl-GHRH$_{(1-44)}$-NH$_2$ or pharmaceutically acceptable salt thereof for use according to item 62, wherein said subject has a fibrosis score of at least 10 prior to the treatment.
64. The trans-3-hexenoyl-GHRH$_{(1-44)}$-NH$_2$ or pharmaceutically acceptable salt thereof for use according to item 62, wherein said subject has a fibrosis score of at least 2 prior to the treatment.
65. The trans-3-hexenoyl-GHRH$_{(1-44)}$-NH$_2$ or pharmaceutically acceptable salt thereof for use according to any one of items 62 to 64, wherein said subject has an HFF of at least about 10%.
66. The trans-3-hexenoyl-GHRH$_{(1-44)}$-NH$_2$ or pharmaceutically acceptable salt thereof for use according to item 65, wherein said subject has an HFF of at least about 15%.
67. The trans-3-hexenoyl-GHRH$_{(1-44)}$-NH$_2$ or pharmaceutically acceptable salt thereof for use according to item 65, wherein said subject has an HFF of at least about 20%.
68. The trans-3-hexenoyl-GHRH$_{(1-44)}$-NH$_2$ or pharmaceutically acceptable salt thereof for use according to any one of items 62 to 67, wherein said subject has serum ALT levels of at least about 30 U/L.
69. The trans-3-hexenoyl-GHRH$_{(1-44)}$-NH$_2$ or pharmaceutically acceptable salt thereof for use according to any one of items 62 to 67, wherein said subject has serum ALT levels of at least about 35 U/L.
70. The trans-3-hexenoyl-GHRH$_{(1-44)}$-NH$_2$ or pharmaceutically acceptable salt thereof for use according to any one of items 62 to 69, wherein said subject has a NAFLD Activity Score (NAS) of at least 2 as measured by the NAS Clinical Research Network (NAS CRN) scoring system.
71. The trans-3-hexenoyl-GHRH$_{(1-44)}$-NH$_2$ or pharmaceutically acceptable salt thereof for use according to item 70, wherein said subject has a NAS of at least 3.
72. The trans-3-hexenoyl-GHRH$_{(1-44)}$-NH$_2$ or pharmaceutically acceptable salt thereof for use according to any one of items 62 to 71, wherein said subject suffers from human immunodeficiency (HIV) infection.
73. The trans-3-hexenoyl-GHRH$_{(1-44)}$-NH$_2$ or pharmaceutically acceptable salt thereof for use according to any one of items 62 to 72, wherein said subject has a body mass index (BMI) of at least about 25.
74. The trans-3-hexenoyl-GHRH$_{(1-44)}$-NH$_2$ or pharmaceutically acceptable salt thereof for use according to item 73, wherein said subject has a BMI of at least about 30.
75. The trans-3-hexenoyl-GHRH$_{(1-44)}$-NH$_2$ or pharmaceutically acceptable salt thereof for use according to any one of items 62 to 74, wherein a pharmaceutically acceptable salt of trans-3-hexenoyl-GHRH$_{(1-44)}$-NH$_2$ is used.
76. The trans-3-hexenoyl-GHRH$_{(1-44)}$-NH$_2$ or pharmaceutically acceptable salt thereof for use according to item 75, wherein said pharmaceutically acceptable salt of trans-3-hexenoyl-GHRH$_{(1-44)}$-NH$_2$ is an acetate salt.
77. The trans-3-hexenoyl-GHRH$_{(1-44)}$-NH$_2$ or pharmaceutically acceptable salt thereof for use according to any one of items 62 to 76, wherein said trans-3-hexenoyl-GHRH$_{(1-44)}$-NH$_2$ or pharmaceutically acceptable salt thereof is for administration at a daily dose of about 1 mg to about 4 mg.
78. The trans-3-hexenoyl-GHRH$_{(1-44)}$-NH$_2$ or pharmaceutically acceptable salt thereof for use according to item 77, wherein said trans-3-hexenoyl-GHRH$_{(1-44)}$-NH$_2$ or pharmaceutically acceptable salt thereof is for administration at a daily dose of about 1 mg to about 2 mg.
79. The trans-3-hexenoyl-GHRH$_{(1-44)}$-NH$_2$ or pharmaceutically acceptable salt thereof for use according to any one of items 62 to 78, wherein said trans-3-hexenoyl-GHRH$_{(1-44)}$-

NH$_2$ or pharmaceutically acceptable salt thereof is for administration by subcutaneous injection.

80. The trans-3-hexenoyl-GHRH$_{(1-44)}$-NH$_2$ or pharmaceutically acceptable salt thereof for use according to any one of items 62 to 79, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

81. The trans-3-hexenoyl-GHRH$_{(1-44)}$-NH$_2$ or pharmaceutically acceptable salt thereof for use according to item 80, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

82. The trans-3-hexenoyl-GHRH$_{(1-44)}$-NH$_2$ or pharmaceutically acceptable salt thereof for use according to item 80, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

83. The method of any one of items 1-20 and 41-61, wherein said trans-3-hexenoyl-GHRH$_{(1-44)}$-NH$_2$ or pharmaceutically acceptable salt thereof is administered for a period of at least 3, 6 or 9 months.

84. The method of item 83, wherein said trans-3-hexenoyl-GHRH$_{(1-44)}$-NH$_2$ or pharmaceutically acceptable salt thereof is administered for a period of at least 12 months.

85. The trans-3-hexenoyl-GHRH$_{(1-44)}$-NH$_2$ or pharmaceutically acceptable salt thereof for use according to any one of items 21-40 and 62-82, wherein said trans-3-hexenoyl-GHRH$_{(1-44)}$-NH$_2$ or pharmaceutically acceptable salt thereof is used for a period of at least 3, 6 or 9 months.

86. The trans-3-hexenoyl-GHRH$_{(1-44)}$-NH$_2$ or pharmaceutically acceptable salt thereof for use according to item 85, wherein said trans-3-hexenoyl-GHRH$_{(1-44)}$-NH$_2$ or pharmaceutically acceptable salt thereof is used for a period of at least 12 months.

87. A method for reducing the risk of developing liver cancer in a subject suffering from nonalcoholic fatty liver (NAFL) or nonalcoholic steatohepatitis (NASH) comprising administering an effective amount of trans-3-hexenoyl-GHRH$_{(1-44)}$-NH$_2$ or a pharmaceutically acceptable salt thereof to said subject.

88. The method of item 87, wherein said method comprises administering an effective amount of a pharmaceutically acceptable salt of trans-3-hexenoyl-GHRH$_{(1-44)}$-NH$_2$ to said subject.

89. The method of item 88, wherein said pharmaceutically acceptable salt of trans-3-hexenoyl-GHRH$_{(1-44)}$-NH$_2$ is an acetate salt.

90. The method of any one of items 87 to 89, wherein said trans-3-hexenoyl-GHRH$_{(1-44)}$-NH$_2$ or pharmaceutically acceptable salt thereof is administered at a daily dose of about 1 mg to about 4 mg.

91. The method of item 90, wherein said trans-3-hexenoyl-GHRH$_{(1-44)}$-NH$_2$ or pharmaceutically acceptable salt thereof is administered at a daily dose of about 1 mg to about 2 mg.

92. The method of any one of items 87 to 91, wherein said trans-3-hexenoyl-GHRH$_{(1-44)}$-NH$_2$ or pharmaceutically acceptable salt thereof is administered by subcutaneous injection.

93. The method of any one of items 87 to 92, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

94. The method of item 93, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

95. The method of item 93, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

96. The method of any one of items 87 to 95, wherein said trans-3-hexenoyl-GHRH$_{(1-44)}$-NH$_2$ or pharmaceutically acceptable salt thereof is administered for a period of at least 3, 6 or 9 months.

97. The method of item 96, wherein said trans-3-hexenoyl-GHRH$_{(1-44)}$-NH$_2$ or pharmaceutically acceptable salt thereof is administered for a period of at least 12 months.

98. Trans-3-hexenoyl-GHRH$_{(1-44)}$-NH$_2$ or a pharmaceutically acceptable salt thereof for use in reducing the risk of developing liver cancer in a subject suffering from nonalcoholic fatty liver (NAFL) or nonalcoholic steatohepatitis (NASH).

99. The trans-3-hexenoyl-GHRH$_{(1-44)}$-NH$_2$ or pharmaceutically acceptable salt thereof for use according to item 98, wherein a pharmaceutically acceptable salt of trans-3-hexenoyl-GHRH$_{(1-44)}$-NH$_2$ is used.

100. The trans-3-hexenoyl-GHRH$_{(1-44)}$-NH$_2$ or pharmaceutically acceptable salt thereof for use according to item 99, wherein said pharmaceutically acceptable salt of trans-3-hexenoyl-GHRH$_{(1-44)}$-NH$_2$ is an acetate salt.

101. The trans-3-hexenoyl-GHRH$_{(1-44)}$-NH$_2$ or pharmaceutically acceptable salt thereof for use according to any one of items 98 to 100, wherein said trans-3-hexenoyl-GHRH$_{(1-44)}$-NH$_2$ or pharmaceutically acceptable salt thereof is for administration at a daily dose of about 1 mg to about 4 mg.

102. The trans-3-hexenoyl-GHRH$_{(1-44)}$-NH$_2$ or pharmaceutically acceptable salt thereof for use according to item 101, wherein said trans-3-hexenoyl-GHRH$_{(1-44)}$-NH$_2$ or pharmaceutically acceptable salt thereof is for administration at a daily dose of about 1 mg to about 2 mg.

103. The trans-3-hexenoyl-GHRH$_{(1-44)}$-NH$_2$ or pharmaceutically acceptable salt thereof for use according to any one of items 98 to 102, wherein said trans-3-hexenoyl-GHRH$_{(1-44)}$-NH$_2$ or pharmaceutically acceptable salt thereof is for administration by subcutaneous injection.

104. The trans-3-hexenoyl-GHRH$_{(1-44)}$-NH$_2$ or pharmaceutically acceptable salt thereof for use according to any one of items 98 to 103, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

105. The trans-3-hexenoyl-GHRH$_{(1-44)}$-NH$_2$ or pharmaceutically acceptable salt thereof for use according to item 104, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

106. The trans-3-hexenoyl-GHRH$_{(1-44)}$-NH$_2$ or pharmaceutically acceptable salt thereof for use according to item 105, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

107. The trans-3-hexenoyl-GHRH$_{(1-44)}$-NH$_2$ or pharmaceutically acceptable salt thereof for use according to any one of items 98 to 106, wherein said trans-3-hexenoyl-GHRH$_{(1-44)}$-NH$_2$ or pharmaceutically acceptable salt thereof is used for a period of at least 3, 6 or 9 months.

108. The trans-3-hexenoyl-GHRH$_{(1-44)}$-NH$_2$ or pharmaceutically acceptable salt thereof for use according to item 107, wherein said trans-3-hexenoyl-GHRH$_{(1-44)}$-NH$_2$ or pharmaceutically acceptable salt thereof is used for a period of at least 12 months.

109. Use of trans-3-hexenoyl-GHRH$_{(1-44)}$-NH$_2$ or a pharmaceutically acceptable salt thereof for the prevention or treatment of nonalcoholic fatty liver (NAFL) or nonalcoholic steatohepatitis (NASH) in a subject, wherein said subject has (i) a hepatic fat fraction (HFF) of at least about 5 or 10% as measured by proton magnetic resonance spectroscopy ($^1$H MRS); (ii) serum alanine aminotransferase (ALT) levels of at least about 25 or 30 U/L; (iii) a NAFLD Activity Score (NAS) of at least 5 as measured by the NAS Clinical Research Network (NAS CRN) scoring system; or (iv) any combination of (i) to (iii).

110. Use of trans-3-hexenoyl-GHRH$_{(1-44)}$-NH$_2$ or a pharmaceutically acceptable salt thereof for the preparation of a medicament for the prevention or treatment of nonalcoholic fatty liver (NAFL) or nonalcoholic steatohepatitis (NASH) in a subject, wherein said subject has (i) a hepatic fat fraction (HFF) of at least about 5 or 10% as measured by proton magnetic resonance spectroscopy ($^1$H MRS); (ii) serum alanine aminotransferase (ALT) levels of at least about 25 or 30 U/L; (iii) a NAFLD Activity Score (NAS) of at least 5 as measured by the NAS Clinical Research Network (NAS CRN) scoring system; or (iv) any combination of (i) to (iii).

111. The use according to item 109 or 110, wherein said subject has an HFF of at least about 5 or 10%.

112. The use according to item 109 or 110, wherein said subject has an HFF of at least about 15%.

113. The use according to item 109 or 110, wherein said subject has an HFF of at least about 20%.

114. The use according to any one of items 109 to 113, wherein said subject has serum ALT levels of at least about 25 or 30 U/L.

115. The use according to any one of items 109 to 114, wherein said subject has serum ALT levels of at least about 35 U/L.

116. The use according to any one of items 109 to 115, wherein said subject has a NAS of at least 6.

117. The use according to item 116, wherein said subject has a NAS of at least 7.

118. The use according to any one of items 109 to 117, wherein said subject has liver fibrosis, for example stage 1A liver fibrosis or worse, preferably stage 10 or stage 2 liver fibrosis or worse.

119. The use according to any one of items 109 to 118, wherein said subject suffers from human immunodeficiency (HIV) infection.

120. The use according to any one of items 109 to 119, wherein said subject has a body mass index (BMI) of at least about 25.

121. The use according to item 120, wherein said subject has a BMI of at least about 30.

122. The use according to any one of items 109 to 121, wherein a pharmaceutically acceptable salt of trans-3-hexenoyl-GHRH$_{(1-44)}$-NH$_2$ is used.

123. The use according to item 122, wherein said pharmaceutically acceptable salt of trans-3-hexenoyl-GHRH$_{(1-44)}$-NH$_2$ is an acetate salt.

124. The use according to any one of items 109 to 123, wherein said trans-3-hexenoyl-GHRH$_{(1-44)}$-NH$_2$ or pharmaceutically acceptable salt thereof is for administration at a daily dose of about 1 mg to about 4 mg.

125. The use according to item 124, wherein said trans-3-hexenoyl-GHRH$_{(1-44)}$-NH$_2$ or pharmaceutically acceptable salt thereof is for administration at a daily dose of about 1 mg to about 2 mg.

126. The use according to any one of items 109 to 125, wherein said trans-3-hexenoyl-GHRH$_{(1-44)}$-NH$_2$ or pharmaceutically acceptable salt thereof is for administration by subcutaneous injection.

127. The use according to any one of items 109 to 126, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

128. The use according to item 127, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

129. The use according to item 127 or 128, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

130. Use of trans-3-hexenoyl-GHRH$_{(1-44)}$-NH$_2$ or a pharmaceutically acceptable salt thereof for (i) preventing or reducing the development or progression of liver fibrosis or (ii) reducing liver fibrosis in a subject.

131. Use of trans-3-hexenoyl-GHRH$_{(1-44)}$-NH$_2$ or a pharmaceutically acceptable salt thereof for the preparation of a medicament for (i) preventing or reducing the development or progression of liver fibrosis or (ii) reducing liver fibrosis in a subject.

132. The use according to item 130 or 131, wherein said subject has a fibrosis score of at least 10 prior to the treatment.

133. The use according to item 130 or 131, wherein said subject has a fibrosis score of at least 2 prior to the treatment.

134. The use according to any one of items 130 to 133, wherein said subject has an HFF of at least about 10%.

135. The use according to item 134, wherein said subject has an HFF of at least about 15%.

136. The use according to item 135, wherein said subject has an HFF of at least about 20%.

137. The use according to any one of items 130 to 136, wherein said subject has serum ALT levels of at least about 30 U/L.

138. The use according to any one of items 130 to 137, wherein said subject has serum ALT levels of at least about 35 U/L.

139. The use according to any one of items 130 to 138, wherein said subject has a NAFLD Activity Score (NAS) of at least 2 as measured by the NAS Clinical Research Network (NAS CRN) scoring system.

140. The use according to item 139, wherein said subject has a NAS of at least 3.

141. The use according to any one of items 130 to 140, wherein said subject suffers from human immunodeficiency (HIV) infection.

142. The use according to any one of items 130 to 141, wherein said subject has a body mass index (BMI) of at least about 25.

143. The use according to item 142, wherein said subject has a BMI of at least about 30.

144. The use according to any one of items 130 to 143, wherein a pharmaceutically acceptable salt of trans-3-hexenoyl-GHRH$_{(1-44)}$-NH$_2$ is used.

145. The use according to item 144, wherein said pharmaceutically acceptable salt of trans-3-hexenoyl-GHRH$_{(1-44)}$-NH$_2$ is an acetate salt.

146. The use according to any one of items 130 to 145, wherein said trans-3-hexenoyl-GHRH$_{(1-44)}$-NH$_2$ or pharmaceutically acceptable salt thereof is for administration at a daily dose of about 1 mg to about 4 mg.

147. The use according to item 146, wherein said trans-3-hexenoyl-GHRH$_{(1-44)}$-NH$_2$ or pharmaceutically acceptable salt thereof is for administration at a daily dose of about 1 mg to about 2 mg.

148. The use according to any one of items 130 to 147, wherein said trans-3-hexenoyl-GHRH$_{(1-44)}$-NH$_2$ or pharmaceutically acceptable salt thereof is for administration by subcutaneous injection.

149. The use according to any one of items 130 to 148, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

150. The use according to item 149, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

151. The use according to item 149 or 150, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

152. Use of trans-3-hexenoyl-GHRH$_{(1-44)}$-NH$_2$ or a pharmaceutically acceptable salt thereof for reducing the risk of developing liver cancer in a subject suffering from nonalcoholic fatty liver (NAFL) or nonalcoholic steatohepatitis (NASH).

153. Use of trans-3-hexenoyl-GHRH$_{(1-44)}$-NH$_2$ or a pharmaceutically acceptable salt thereof for the preparation of a medicament for reducing the risk of developing liver cancer in a subject suffering from nonalcoholic fatty liver (NAFL) or nonalcoholic steatohepatitis (NASH).

154. The use according to item 152 or 153, wherein a pharmaceutically acceptable salt of trans-3-hexenoyl-GHRH$_{(1-44)}$-NH$_2$ is used.

155. The use according to item 154, wherein said pharmaceutically acceptable salt of trans-3-hexenoyl-GHRH$_{(1-44)}$-NH$_2$ is an acetate salt.

156. The use according to any one of items 152 to 155, wherein said trans-3-hexenoyl-GHRH$_{(1-44)}$-NH$_2$ or pharmaceutically acceptable salt thereof is for administration at a daily dose of about 1 mg to about 4 mg.

157. The use according to item 156, wherein said trans-3-hexenoyl-GHRH$_{(1-44)}$-NH$_2$ or pharmaceutically acceptable salt thereof is for administration at a daily dose of about 1 mg to about 2 mg.

158. The use according to any one of items 152 to 157, wherein said trans-3-hexenoyl-GHRH$_{(1-44)}$-NH$_2$ or pharmaceutically acceptable salt thereof is for administration by subcutaneous injection.

159. The use according to any one of items 152 to 158, wherein said trans-3-hexenoyl-GHRH$_{(1-44)}$-NH$_2$ or pharmaceutically acceptable salt thereof is present in a pharmaceutical composition comprising at least one pharmaceutically acceptable excipient.

160. The use according to item 159, wherein the concentration of trans-3-hexenoyl-GHRH$_{(1-44)}$-NH$_2$ or pharmaceutically acceptable salt thereof in the pharmaceutical composition is about 1 mg/mL to about 10 mg/mL.

161. The use according to item 159 or 160, wherein the concentration of trans-3-hexenoyl-GHRH$_{(1-44)}$-NH$_2$ or pharmaceutically acceptable salt thereof in the pharmaceutical composition is about 1 mg/mL to about 8 mg/mL.

162. The use according to any one of items 109 to 161, wherein said trans-3-hexenoyl-GHRH$_{(1-44)}$-NH$_2$ or pharmaceutically acceptable salt thereof is for use for a period of at least 3, 6 or 9 months.

163. The use according to item 162, wherein said trans-3-hexenoyl-GHRH$_{(1-44)}$-NH$_2$ or pharmaceutically acceptable salt thereof is for use for a period of at least 12 months.

Other objects, advantages and features of the present disclosure will become more apparent upon reading of the following non-restrictive description of specific embodiments thereof, given by way of example only with reference to the accompanying drawings.

BRIEF DESCRIPTION OF DRAWINGS

In the appended drawings:

FIG. 2 is a table showing the effects of tesamorelin on hepatic fat, metabolic, and immunologic indices.

DETAILED DESCRIPTION

Figure 1:
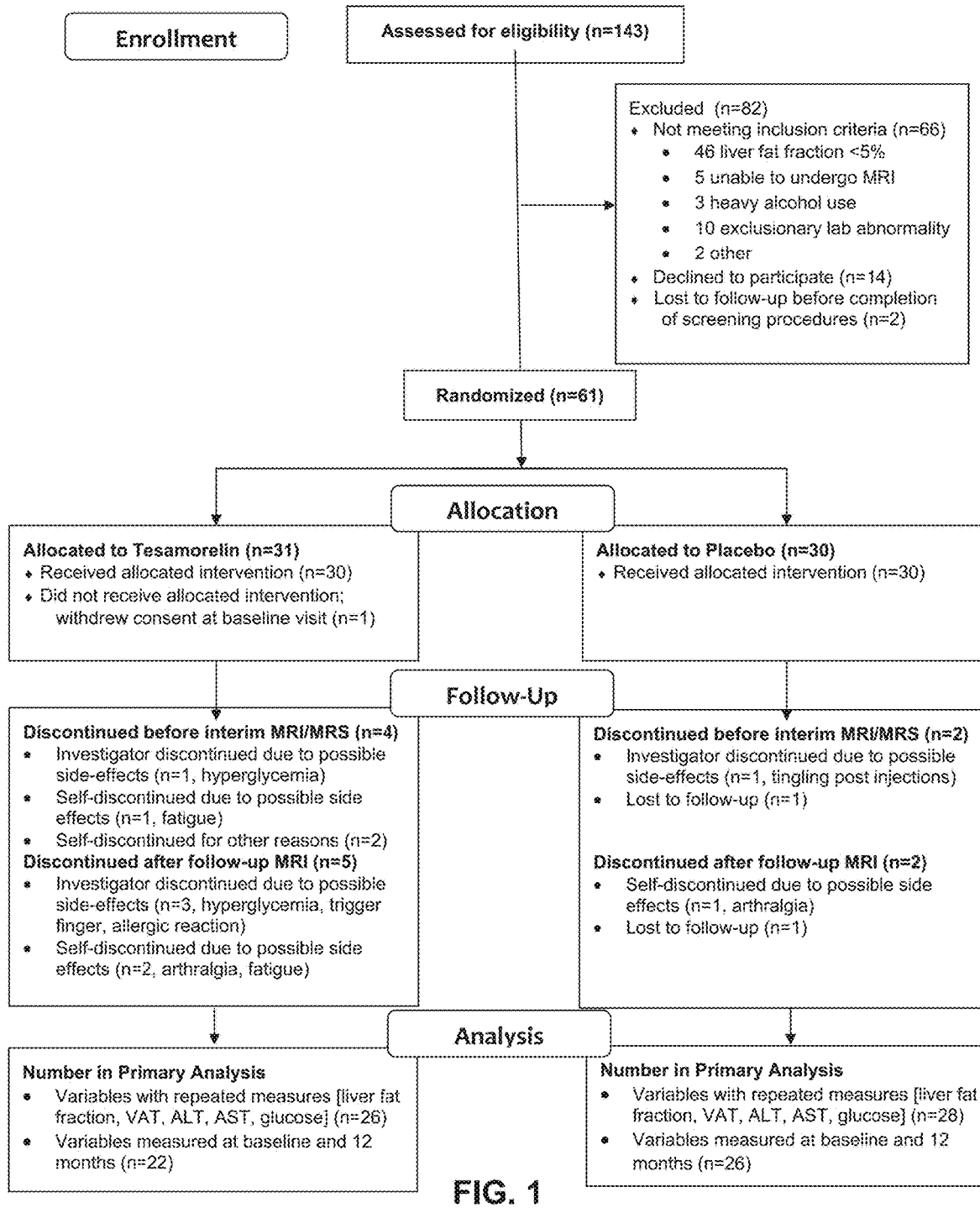
FIG. 1 is a diagram showing the participant flow and reasons for patient exclusion from the study.

The use of the terms "a" and "an" and "the" and similar referents in the context of describing the subject matter (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein.

Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language ("e.g.", "such as") provided herein, is intended merely to better illustrate the disclosure and does not pose a limitation on the scope of the disclosure unless otherwise claimed.

Herein, the term "about" has its ordinary meaning. The term "about" is used to indicate that a value includes an inherent variation of error for the device or the method being employed to determine the value, or encompass values close to the recited values, for example within 10% of the recited values (or range of values).

Unless otherwise defined, all technical and scientific terms used herein have the same meaning as commonly understood by one of ordinary skill in the art to which this disclosure belongs.

In the studies described herein, it is shown that administration of tesamorelin (trans-3-hexenoyl-GHRH$_{(1-44)}$-NH$_2$, acetate salt) significantly reduces and/or normalizes liver fat content and prevents progression of liver fibrosis in HIV-infected subjects with NAFL/NASH with or without fibrosis. The results provide evidence that the beneficial effects of tesamorelin treatment are more prominent in subjects having high NAFLD Activity Score (NAS) prior to treatment, i.e. subjects having more advanced or severe disease. In view of the fact that the fibrosis stage is the strongest predictor of mortality in patients with NAFLD and that a high percentage of HIV patients with NAFLD demonstrate progression of fibrosis over 1 year, the prevention of liver fibrosis by tesamorelin treatment in patients with high NAS shown in the present study is clinically important. Furthermore, Tesamorelin was unexpectedly shown to have a more pronounced effect on the reduction of liver fat relative to visceral fat. Gene expression analyses revealed that administration of tesamorelin was associated with upregulation of genes pertaining to oxidative phosphorylation and genes associated with good prognosis of hepatocellular carcinoma (HCC), and down-regulation of genes pertaining to hepatic inflammation, tissue repair, cell turnover, and poor prognosis of HCC.

In an aspect, the present disclosure provides a method for treating NAFL or NASH with or without fibrosis in a subject in need thereof comprising administering an effective amount of a GHRH molecule or a pharmaceutically acceptable salt thereof, preferably trans-3-hexenoyl-GHRH$_{(1-44)}$-NH$_2$ or a pharmaceutically acceptable salt thereof, to said subject, wherein said subject has (i) a hepatic fat fraction (HFF) of at least 5, 6, 7, 8, 9 or 10% (for example as measured by proton magnetic resonance spectroscopy ($^1$H MRS)); (ii) serum alanine aminotransferase (ALT) levels of at least 25, 26, 27, 28, 29 or 30 U/L; (iii) a NAS of at least 1, 2, 3, 4 or 5, preferably at least 3, 4 or 5, as measured by the NAS Clinical Research Network (NAS CRN) scoring system; (iv) liver fibrosis, e.g., stage 1A, 1B, 1C, 2, 3 liver fibrosis or worse; or (v) any combination of (i) to (iv).

In another aspect, the present disclosure provides a method for treating NAFL or NASH in a subject having a hepatic fat fraction (HFF) of at least about 5 or 10% (for example as measured by proton magnetic resonance spectroscopy ($^1$H MRS)), said method comprising administering an effective amount of a GHRH molecule or a pharmaceutically acceptable salt thereof, preferably trans-3-hexenoyl-GHRH$_{(1-44)}$-NH$_2$ or a pharmaceutically acceptable salt thereof, to said subject. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for treating NAFL or NASH in a subject having a HFF of at least about 5 or 10% (for example as measured by $^1$H MRS). The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for the manufacture of a medicament for treating NAFL or NASH in a subject having a HFF of at least about 5 or 10% (for example as measured $^1$H MRS). The present disclosure also provides a GHRH molecule or a pharmaceutically acceptable salt thereof, preferably trans-3-hexenoyl-GHRH$_{(1-44)}$-NH$_2$ or a pharmaceutically acceptable salt thereof, for use in the treatment of NAFL or NASH in a subject having a HFF of at least about 5 or 10% (for example as measured by proton magnetic resonance spectroscopy ($^1$H MRS)).

In another aspect, the present disclosure provides a method for treating NAFL or NASH in a subject having serum ALT levels at least about 25 or 30 U/L, said method comprising administering an effective amount of a GHRH molecule or a pharmaceutically acceptable salt thereof, preferably trans-3-hexenoyl-GHRH$_{(1-44)}$-NH$_2$ or a pharmaceutically acceptable salt thereof, to said subject. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for treating NAFL or NASH in a subject having serum ALT levels at least about 25 or 30 U/L. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for the manufacture of a medicament for treating NAFL or NASH in a subject having serum ALT levels at least about 25 or 30 U/L. The present disclosure also provides a GHRH molecule or a pharmaceutically acceptable salt thereof, preferably trans-3-hexenoyl-GHRH$_{(1-44)}$-NH$_2$ or a pharmaceutically acceptable salt thereof, for use in the treatment of NAFL or NASH in a subject having serum ALT levels at least about 25 or 30 U/L.

In another aspect, the present disclosure provides a method for (i) preventing or reducing the development or progression of liver fibrosis or (ii) reducing liver fibrosis in a subject suffering from NAFL or NASH with or without fibrosis, said method comprising administering an effective amount of a GHRH molecule or a pharmaceutically acceptable salt thereof, preferably trans-3-hexenoyl-GHRH$_{(1-44)}$-NH$_2$ or a pharmaceutically acceptable salt thereof, to said subject. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for (i) preventing or reducing the development or progression of liver fibrosis or (ii) reducing liver fibrosis in a subject suffering from NAFL or NASH with or without fibrosis. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for the manufacture of a medicament for (i) preventing or reducing the development or progression of liver fibrosis or (ii) reducing liver fibrosis in a subject suffering from NAFL or NASH with or without fibrosis. The present disclosure also provides a GHRH molecule or a pharmaceutically acceptable salt thereof, preferably trans- 3-hexenoyl-GHRH$_{(1-44)}$-NH$_2$ or a pharmaceutically acceptable salt thereof, for use in (i) preventing the development or progression of liver fibrosis or (ii) reducing liver fibrosis in a subject suffering from NAFL or NASH with or without fibrosis.

In another aspect, the present disclosure provides a method for maintaining or reducing the NAS in a subject suffering from NAFL or NASH and having a NAS of at least 1, 2, 3, 4 or 5, preferably at least 3, 4 or 5, as measured by the NAS CRN scoring system, said method comprising administering an effective amount of a GHRH molecule or a pharmaceutically acceptable salt thereof, preferably trans-3-hexenoyl-GHRH$_{(1-44)}$-NH$_2$ or a pharmaceutically acceptable salt thereof, to said subject. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for maintaining or reducing the NAS in a subject suffering from NAFL or NASH with or without fibrosis and having a NAS of at least 1, 2, 3, 4 or 5, preferably at least 3, 4 or 5, as measured by the NAS CRN scoring system. The present disclosure also provides the use of a GHRH molecule or a pharmaceutically acceptable salt thereof, preferably trans-3-hexenoyl-GHRH$_{(1-44)}$-NH$_2$ or a pharmaceutically acceptable salt thereof, for the manufacture of a medicament for maintaining or reducing the NAS in a subject suffering from NAFL or NASH with or without fibrosis and having a NAS of at least 1, 2, 3, 4 or 5, preferably at least 3, 4 or 5, as measured by the NAS CRN scoring system. The present disclosure also provides a GHRH molecule or a pharmaceutically acceptable salt thereof, preferably trans-3-hexenoyl-GHRH$_{(1-44)}$-NH$_2$ or a pharmaceutically acceptable salt thereof, for use in maintaining or reducing the NAS in a subject suffering from NAFL or NASH with or without fibrosis and having a NAS of at least 1, 2, 3, 4 or 5, preferably at least 3, 4 or 5, as measured by the NAS CRN scoring system.

In another aspect, the present disclosure provides a method for reducing the risk or likelihood of developing liver cancer in a subject suffering from NAFL or NASH comprising administering an effective amount of trans-3-hexenoyl-GHRH$_{(1-44)}$-NH$_2$ or a pharmaceutically acceptable salt thereof to said subject. The present disclosure also provides Trans-3-hexenoyl-GHRH$_{(1-44)}$-NH$_2$ or a pharmaceutically acceptable salt thereof for reducing the risk or likelihood of developing liver cancer in a subject suffering from NAFL or NASH. The present disclosure also provides the use of trans-3-hexenoyl-GHRH$_{(1-44)}$-NH$_2$ or a pharmaceutically acceptable salt thereof for reducing the risk or likelihood of developing liver cancer in a subject suffering from NAFL or NASH, or for the manufacture of a medicament for reducing the risk or likelihood of developing liver cancer in a subject suffering from NAFL or NASH. In an embodiment, the liver cancer is hepatocellular carcinoma (HCC).

In an embodiment, the above-mentioned subject has an HFF of at least about 5, 6, 7, 8, 9 or 10% as measured for example by $^1$H MRS. In an embodiment, the above-mentioned subject has an HFF of at least about 11% as measured for example by $^1$H MRS. In an embodiment, the subject has an HFF of at least about 12% as measured for example by $^1$H MRS. In an embodiment, the subject has an HFF of at least about 13% as measured for example by $^1$H MRS. In an embodiment, the subject has an HFF of at least about 14% as measured for example by $^1$H MRS. In an embodiment, the subject has an HFF of at least about 15% as measured for example by $^1$H MRS. In an embodiment, the subject has an HFF of at least about 16% as measured for example by $^1$H MRS. In an embodiment, the subject has an HFF of at least about 17% as measured for example by $^1$H MRS. In an embodiment, the subject has an HFF of at least about 18% as measured for example by $^1$H MRS. In an embodiment, the subject has an HFF of at least about 19% as measured for example by $^1$H MRS. In an embodiment, the subject has an HFF of at least about 20% as measured for example by $^1$H MRS. In an embodiment, the subject has an HFF of at least about 21% as measured for example by $^1$H MRS. In an embodiment, the subject has an HFF of at least about 22% as measured for example by $^1$H MRS. In an embodiment, the subject has an HFF of at least about 23% as measured for example by $^1$H MRS. In an embodiment, the subject has an HFF of at least about 24% as measured for example by $^1$H MRS. In an embodiment, the subject has an HFF of at least about 25% as measured for example by $^1$H MRS. In an embodiment, the subject has an HFF of at least about 30% as measured for example by $^1$H MRS. In an embodiment, the subject has an HFF of at least about 35% as measured for example by $^1$H MRS.

In an embodiment, the above-mentioned method or use comprises identifying a subject having an HFF of at least about 10%, 11%, 12%, 13%, 14%, 15%, 16%, 17%, 18%, 19%, 20%, 21%, 22%, 23%, 24%, 25%, 30%, or 35%, as measured for example by $^1$H MRS.

In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, results in no significant change (i.e. stabilization or normalization), or a reduction, of HFF.

In another embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least about 35% (relative reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least about 40% (relative reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least about 45% (relative reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least about 50% (relative reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least two-fold. In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least three-fold. In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 4-fold. In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 5-fold.

In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 4% or 5% (absolute reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 6% (absolute reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 7% (absolute reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 8% (absolute reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 9% (absolute reduction). In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces HFF by at least 10% (absolute reduction).

In an embodiment, the above-mentioned subject has a NAS of at least 1 as measured by the NAS CRN scoring system. In an embodiment, the above-mentioned subject has a NAS of at least 2 as measured by the NAS CRN scoring system. In an embodiment, the above-mentioned subject has a NAS of at least 3 as measured by the NAS CRN scoring system. In an embodiment, the above-mentioned subject has a NAS of at least 4 as measured by the NAS CRN scoring system. In an embodiment, the above-mentioned subject has a NAS of at least 5 as measured by the NAS CRN scoring system. In an embodiment, the subject has a NAS of at least 6 as measured by the NAS CRN scoring system. In an embodiment, the subject has a NAS of at least 7 as measured by the NAS CRN scoring system. In an embodiment, the subject has a NAS of 8 as measured by the NAS CRN scoring system. The NAS calculated according to the NAS CRN scoring system comprises the sum of grades for steatosis (grades 0-3), hepatocellular ballooning (grades 0-2), and lobular inflammation (grades 0-3) (Kleiner D E, et al. Hepatology 2005; 41:1313-21). In an embodiment, the treatment reduces the steatosis score. In an embodiment, the treatment reduces the hepatocellular ballooning score. In an embodiment, the treatment reduces the lobular inflammation score. In an embodiment, the treatment reduces at least two of the steatosis score, the hepatocellular ballooning score and the lobular inflammation score.

In an embodiment, the above-mentioned method or use comprises identifying a subject having a NAS of at least 1, 2, 3, 4, 5, 6, 7 or 8 as measured by the NAS CRN scoring system.

In another embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, results in no significant change (i.e. stabilization or normalization) or a reduction of the NAS over time. In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, results in a reduction of the NAS score. In an embodiment, the reduction of the NAS score is a reduction of at least 0.2. In a further embodiment, the reduction of the NAS score is a reduction of at least 0.3. In a further embodiment, the reduction of the NAS score is a reduction of at least 0.4. In a further embodiment, the reduction of the NAS score is a reduction of at least 0.5. In a further embodiment, the reduction of the NAS score is a reduction of at least 0.6. In a further embodiment, the reduction of the NAS score is a reduction of at least 0.7. In a further embodiment, the reduction of the NAS score is a reduction of at least 0.8. In a further embodiment, the reduction of the NAS score is a reduction of at least 0.9. In a further embodiment, the reduction of the NAS score is a reduction of at least 1.0. In a further embodiment, the reduction of the NAS score is a reduction of at least 2.0.

In an embodiment, the above-mentioned subject has serum ALT levels of at least about 30 U/L. In an embodiment, the above-mentioned subject has serum ALT levels of at least about 35 U/L. In another embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces serum ALT levels by at least about 10%, 15%, 20%, 25% or 30% in the subject.

In an embodiment, the above-mentioned method or use comprises identifying a subject having serum ALT levels of at least about 25, 30 U/L or 35 U/L.

In another embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces serum C-reactive protein (CRP) levels in the subject.

In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces inflammation and/or oxidative stress (e.g., the level of reactive oxygen (ROS) species) in the liver of the subject. In an embodiment, the reduction of inflammation comprises a reduction of the activation of inflammatory pathways (e.g., TNF-alpha, IL-6 and/or IL-2 pathways) or inflammatory-related genes.

In an embodiment, the administration of the GHRH molecule or a pharmaceutically acceptable salt thereof, preferably trans-3-hexenoyl-GHRH$_{(1-44)}$-NH$_2$ or pharmaceutically acceptable salt thereof, reduces tissue repair in the liver, e.g., reduces the expression of genes involved in tissue repair, cell apoptosis, and/or Epithelial to mesenchymal transition (EMT), such as genes from the TGF-β pathway.

In an embodiment, the subject suffers from human immunodeficiency virus (HIV) infection.

In an embodiment, the subject is undergoing antiretroviral therapy.

In an embodiment, the treatment or use described herein has no or substantially no effect on low-density lipoprotein cholesterol (LDL-C), high-density lipoprotein cholesterol (HDL-C), or triglycerides in the subject. In an embodiment, the treatment or use described herein has no or substantially no effect on fasting glucose or hemoglobin A1c in the subject.

In an embodiment, the subject has a body mass index (BMI) of at least about 25. In an embodiment, the subject has a BMI of at least about 26. In an embodiment, the subject has a BMI of at least about 27. In an embodiment, the subject has a BMI of at least about 28. In an embodiment, the subject has a BMI of at least about 29. In an embodiment, the subject has a BMI of at least about 30. In an embodiment, the subject has a BMI of at least about 31. In an embodiment, the subject has a BMI of at least about 32.

In an embodiment, the above-mentioned subject has liver fibrosis. In an embodiment, the above-mentioned method or use comprises identifying a subject having liver fibrosis. In an embodiment, the above-mentioned subject has stage 1 (in a further embodiment, stage 1A, 1B or 1C) liver fibrosis. In an embodiment, the above-mentioned subject has stage 2 liver fibrosis. In an embodiment, the above-mentioned subject has stage 3 liver fibrosis. The fibrosis stage is determined using the scoring system devised by the Pathology Committee of the NASH Clinical Research Network (Kleiner D E, et al. *Hepatology* 2005; 41:1313-21):
  Stage 0=no fibrosis;
  Stage 1=Perisinusoidal or periportal fibrosis;
  Stage 1A: Mild, zone 3, perisinusoidal;
  Stage 1B: Moderate, zone 3, perisinusoidal;
  Stage 1C: Portal/periportal only;
  Stage 2=Both perisinusoidal and portal/periportal;
  Stage 3=Bridging fibrosis;
  Stage 4=Cirrhosis.

In an embodiment, the above-mentioned subject has at least two of the following features (1) to (3): (1) an HFF of at least 15%, preferably of at least 20%, 25% or 30%; (2) a NAS score of at least 3, preferably of at least 4, 5 or 6; and (3) liver fibrosis, preferably stage 1C or 2 liver fibrosis or worse. In an embodiment, the above-mentioned subject has features (1) to (3) noted above. In an embodiment, the above-mentioned method or use comprises identifying a subject having at least two, or all of the above-mentioned features (1) to (3).

Preventing progression as used herein in reference to liver fibrosis, refers to no or substantially no progression of liver fibrosis following treatment with a GHRH molecule relative to in the absence of such treatment. Reducing progression as used herein in reference to liver fibrosis, refers to a situation in which progression of liver fibrosis may continue following treatment with a GHRH molecule, however at a reduced rate of progression relative to in the absence of such treatment.

In an embodiment, the treatment or use described herein reduces the risk or likelihood that the subject develops liver cancer such as hepatocellular carcinoma (HCC).

The term "GHRH molecule" as used in the context of the present disclosure includes, without limitation, human native GHRH$_{(1-44)}$ and fragments thereof (e.g., GHRH$_{(1-40)}$, GHRH$_{(1-29)}$, fragments ranging between 1-29 and the 1-44 sequence), and any other fragments; GHRH from other species and fragments thereof; GHRH variants containing amino acid(s) substitution(s), addition(s) and/or deletion(s); derivatives or analogs of GHRH or fragments or variants thereof having for example an organic group or a moiety coupled to the GHRH amino acid sequence at the N-terminus, the C-terminus or on the side-chain; and pharmaceutically acceptable salts of GHRH (human or from other species), as well as pharmaceutically acceptable salts of GHRH fragments, variants, analogs and derivatives. The GHRH molecules of the present disclosure also encompass the GHRH molecules currently known in the art, including, without limitation, albumin-conjugated GHRH (U.S. Pat. No. 7,268,113); pegylated GHRH peptide (U.S. Pat. Nos. 7,256,258 and 6,528,485); porcine GHRH (1-40) (U.S. Pat. No. 6,551,996); canine GHRH (U.S. patent application No. 2005/0064554); GHRH variants of 1-29 to 1-44 amino acid length (U.S. Pat. Nos. 5,846,936, 5,696,089, 5,756,458 and 5,416,073, and U.S. patent application Nos. 2006/0128615 and 2004/0192593); and Pro⁰-GHRH peptide and variants thereof (U.S. Pat. No. 5,137,872).

The GHRH analogs include those described in U.S. Pat. Nos. 5,681,379 and 5,939,386, which also describe their method of synthesis. More particularly, these GHRH analogs are defined by the following formula A:

X-GHRH Peptide  (A)

wherein the GHRH peptide is a peptide of the following formula B (SEQ ID NO:2):

A1-A2-Asp-Ala-Ile-Phe-Thr-A8-Ser-Tyr-Arg-Lys-
  A13-Leu-A15-Gln-Leu-A18-Ala-Arg-Lys-Leu-
  Leu-A24-A25-Ile-A27-A28-Arg-A30-A31-A32-
  A33-A34-A35-A36-A37-A38-A39-A40-A41-
  A42-A43-A44-R0  (B)

wherein,
  A1 is Tyr or His;
  A2 is Val or Ala;
  A8 is Asn or Ser;
  A13 is Val or Ile;
  A15 is Ala or Gly;
  A18 is Ser or Tyr;
  A24 is Gln or His;
  A25 is Asp or Glu;
  A27 is Met, Ile or Nle
  A28 is Ser or Asn;
  A30 is absent or is any amino acid, preferably Gln;
  A31 is absent or is any amino acid, preferably Gln;
  A32 is absent or is any amino acid, preferably Gly;
  A33 is absent or is any amino acid, preferably Glu;
  A34 is absent or is any amino acid, preferably Ser;
  A35 is absent or is any amino acid, preferably Asn;
  A36 is absent or is any amino acid, preferably Gln;
  A37 is absent or is any amino acid, preferably Glu;
  A38 is absent or is any amino acid, preferably Arg;
  A39 is absent or is any amino acid, preferably Gly;
  A40 is absent or is any amino acid, preferably Ala;
  A41 is absent or is any amino acid, preferably Arg;
  A42 is absent or is any amino acid, preferably Ala;
  A43 is absent or is any amino acid, preferably Arg;
  A44 is absent or is any amino acid, preferably Leu; and
  R0 is NH$_2$ or NH—(CH$_2$)n-CONH$_2$, with n=1 to 12.

The group X is a hydrophobic tail anchored via an amide bond to the N-terminus of the peptide and the hydrophobic tail defining a backbone of 5 to 7 atoms. The backbone can be substituted by C$_{1-6}$ alkyl, C$_{3-6}$ cycloalkyl, or C$_{6-12}$ aryl and the backbone comprises at least one rigidifying moiety connected to at least two atoms of the backbone. The rigidifying moiety is a double bond, triple bond, saturated or unsaturated C$_{3-9}$ cycloalkyl, or C$_{6-12}$ aryl.

In an embodiment, group X is:

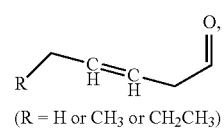

(R = H or CH$_3$ or CH$_2$CH$_3$)

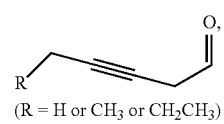

(R = H or CH$_3$ or CH$_2$CH$_3$)

-continued

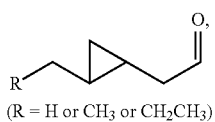
(R = H or CH₃ or CH₂CH₃)

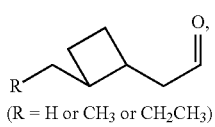
(R = H or CH₃ or CH₂CH₃)

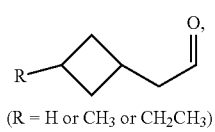
(R = H or CH₃ or CH₂CH₃)

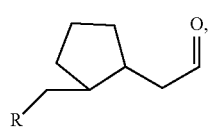
(R = H or CH₃ or CH₂CH₃)

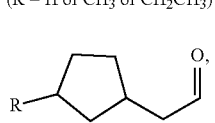
(R = H or CH₃ or CH₂CH₃)

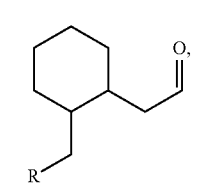
(R = H or CH₃ or CH₂CH₃)

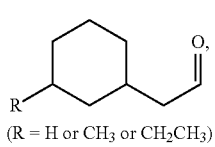
(R = H or CH₃ or CH₂CH₃)

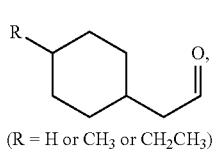
(R = H or CH₃ or CH₂CH₃)

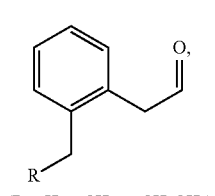
(R = H or CH₃ or CH₂CH₃)

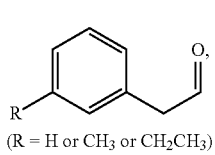
(R = H or CH₃ or CH₂CH₃)

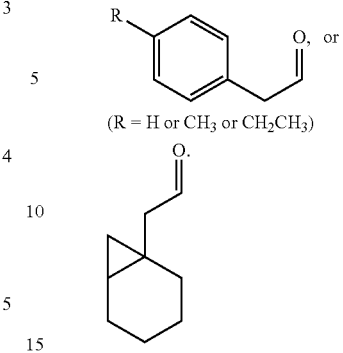
(R = H or CH₃ or CH₂CH₃)

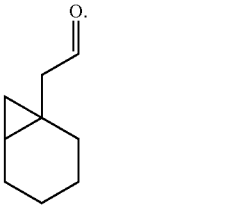

In an embodiment, in formula B, A30-A44 are: (a) absent; (b) an amino acid sequence corresponding to positions 30-44 of a native GHRH peptide (SEQ ID NO: 3), or (c) the amino acid sequence of (b) having a 1-14 amino acid deletion from its C-terminus.

In an embodiment, the GHRH peptide is a polypeptide comprising the amino acid sequence of SEQ ID NO: 4.

Figure 5:
FIG. 5 shows the structure of tesamorelin (trans-3-hexenoyl-GHRH$_{(1-44)}$-NH$_2$; SEQ ID NO: 1).

In an embodiment, the GHRH molecule is (hexenoyl trans-3)hGHRH$_{(1\text{-}44)}$NH$_2$ (SEQ ID NO: 1) or a pharmaceutically acceptable salt thereof. [trans-3-hexenoyl] hGHRH$_{(1\text{-}44)}$ amide (also referred to as tesamorelin and (hexenoyl trans-3)hGHRH$_{(1\text{-}44)}$NH$_2$) is a synthetic human GHRH (hGHRH) analog that comprises the 44-amino acid sequence of hGHRH on which a hexenoyl moiety, a C$_6$ side chain, has been anchored on the amino-terminal tyrosine residue. The structure of [trans-3-hexenoyl]hGHRH$_{(1\text{-}44)}$ amide is depicted at FIG. 5.

The term "pharmaceutically acceptable salt" refers to a salt of a GHRH molecule (e.g., trans-3-hexenoyl-GHRH$_{(1\text{-}44)}$-NH$_2$) that is pharmacologically acceptable and substantially non-toxic to the subject to which it is administered. More specifically, these salts retain the biological effectiveness and properties of the GHRH molecules (e.g., trans-3-hexenoyl-GHRH$_{(1\text{-}44)}$-NH$_2$) and are formed from suitable non-toxic organic or inorganic acids or bases.

For example, these salts include acid addition salts of GHRH molecules (e.g., trans-3-hexenoyl-GHRH$_{(1\text{-}44)}$-NH$_2$) which are sufficiently basic to form such salts. Such acid addition salts include acetates, adipates, alginates, lower alkanesulfonates such as a methanesulfonates, trifluoromethanesulfonates or ethanesulfonates, arylsulfonates such as a benzenesulfonates, 2-naphthalenesulfonates, or toluenesulfonates (also known as tosylates), ascorbates, aspartates, benzoates, benzenesulfonates, bisulfates, borates, butyrates, citrates, camphorates, camphorsulfonates, cinnamates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydrogen sulphates, 2-hydroxyethanesulfonates, itaconates, lactates, maleates, mandelates, methanesulfonates, nicotinates, nitrates, oxalates, pamoates, pectinates, perchlorates, persulfates, 3-phenylpropionates, phosphates, picrates, pivalates, propionates, salicylates, succinates, sulfates, sulfonates, tartrates, thiocyanates, undecanoates and the like.

Additionally, acids which are generally considered suitable for the formation of pharmaceutically useful salts from basic pharmaceutical compounds are discussed, for example, by P. Stahl et al., Camille G. (eds.) *Handbook of*

*Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website).

Such salts can be formed quite readily by those skilled in the art using standard techniques. Indeed, the chemical modification of a pharmaceutical compound (i.e. drug) into a salt is a technique well known to pharmaceutical chemists, (See, e.g., H. Ansel et. al., Pharmaceutical Dosage Forms and Drug Delivery Systems ($6^{th}$ Ed. 1995) at pp. 196 and 1456-1457). Salts of the trans-3-hexenoyl-GHRH$_{(1-44)}$-NH$_2$ may be formed, for example, by reacting the trans-3-hexenoyl-GHRH$_{(1-44)}$-NH$_2$ with an amount of acid or base, such as an equivalent amount, in a medium such as one in which the salt precipitates or in an aqueous medium followed by lyophilization.

In an embodiment, the pharmaceutically acceptable salt of the GHRH molecule, preferably trans-3-hexenoyl-GHRH$_{(1-44)}$-NH$_2$, is an acetate salt.

In an embodiment, the GHRH molecule, preferably trans-3-hexenoyl-GHRH$_{(1-44)}$-NH$_2$, or pharmaceutically acceptable salt thereof is present in a pharmaceutical composition at a dose of about 1 mg/ml to about 10 mg/ml. In a further embodiment, the GHRH molecule, preferably trans-3-hexenoyl-GHRH$_{(1-44)}$-NH$_2$, or pharmaceutically acceptable salt thereof is present in a pharmaceutical composition at a dose of about 1 mg/ml to about 10 mg/ml, preferably about 1 mg/ml to about 8 mg/ml or about 4 mg/ml to about 8 mg/ml, for example about 1 mg/ml, about 2 mg/ml, about 3 mg/ml, about 4 mg/ml, about 5 mg/ml, about 6 mg/ml, about 7 mg/ml, or about 8 mg/ml.

In an embodiment, the GHRH molecule, preferably trans-3-hexenoyl-GHRH$_{(1-44)}$-NH$_2$, or pharmaceutically acceptable salt thereof is present in a pharmaceutical composition comprising one or more pharmaceutically acceptable excipients.

The term "pharmaceutically acceptable excipient" as used herein has its normal meaning in the art and is any ingredient that is not an active ingredient (drug) itself. Excipients include for example binders, lubricants, diluents, bulking agents (fillers), thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art, and the present composition is not limited in these respects. In certain embodiments, the pharmaceutical composition comprises one or more excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive. Therapeutic formulations are prepared using standard methods known in the art by mixing the active ingredient having the desired degree of purity with one or more optional pharmaceutically acceptable carriers, excipients and/or stabilizers. The excipient(s) may be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration (see Remington: *The Science and Practice of Pharmacy*, by Loyd V Allen, Jr, 2012, $22^{nd}$ edition, Pharmaceutical Press; *Handbook of Pharmaceutical Excipients*, by Rowe et al., 2012, $7^{th}$ edition, Pharmaceutical Press). In an embodiment, the pharmaceutical composition is an injectable composition. In an embodiment, the pharmaceutical composition comprises one or more excipients for subcutaneous administration/injection.

In an embodiment, the pharmaceutical composition comprises a bulking agent. The term "bulking agent" as used herein refers to a compound used to provide an adequate or desired tonicity of the solution resulting from the reconstitution of the lyophilized formulation. Preferably, the adequate or desired tonicity of the solution is equal to or approximates isotonicity with physiological fluid of the subject to which the solution is administered. For example, one or more sugars may be used as the bulking agent. Sugars, as used herein, include, but are not limited to, monosaccharides, oligosaccharides and polysaccharides. Examples of suitable sugars include, but are not limited to, mannose, sorbose, xylose, maltose, lactose, sucrose, and dextran. Sugar also includes sugar alcohols, such as mannitol, inositol, dulcitol, xylitol and arabitol. Mixtures of sugars may also be used in accordance with the present disclosure. In an embodiment, the bulking agent is mannitol. For example, one or more amino acids, such as glycine, may be used as the bulking agent. The bulking agent is in concentration of about 1% to about 10% (w/w) or about 2% to about 8% (w/w) in the pharmaceutical composition. In an embodiment, the bulking agent is in concentration of about 3 to about 5% (w/w) in the pharmaceutical composition. In a further embodiment, the bulking agent is in concentration of about 4% (w/w) in the pharmaceutical composition.

In an embodiment, the pharmaceutical composition of the present disclosure may further comprise a surfactant. Typical examples of surfactants include sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide; alkyl sulfates having a $C_{10-18}$ alkyl group such as sodium cetyl sulfate, sodium lauryl sulfate, sodium oleyl sulfate; polyoxyethylene alkyl ether sulfates having an average EO mole number of 2-4 and a $C_{10-18}$ alkyl group such as sodium polyoxyethylene lauryl sulfate; alkyl sulfosuccinic acid ester salts having a $C_{8-18}$ alkyl group such as sodium laurylsulfosuccinate; lecithin; glycerophospholipids; sphingophospholipids such as sphingomyelin; sucrose fatty acid esters of $C_{12-18}$ fatty acids.

In an embodiment, the surfactant is a non-ionic surfactant. In a further embodiment, the surfactant is polyoxyethylene sorbitan alkyl ester. In yet a further embodiment, the surfactant is polysorbate-20 (T20 or Tween-20™).

In an embodiment, the pharmaceutical composition of the present disclosure may further comprise one or more stabilizing agents or stabilizers. As used herein, the term "stabilizer" is intended to mean a compound used to stabilize the therapeutic agent against physical, chemical, or biochemical process that would reduce the therapeutic activity of the agent. Suitable stabilizers are non-reducing sugars including, by way of example and without limitation, sucrose (or saccharose) and trehalose; and non-reducing polyols including, by way of example and without limitation, sorbitol, mannitol, maltitol, xylitol, glycol, glycerol and ethylene glycol. In an embodiment, the pharmaceutical composition comprises about 2% to about 10% (w/v) of mannitol. In a further embodiment, the pharmaceutical composition comprises about 2% to about 8% (w/v), about 3% to about 7% (w/v), about 4% to about 6% (w/v), or about 5% (w/v), of mannitol.

In an embodiment, the pharmaceutical composition of the present disclosure comprises a non-reducing sugar. "Non-reducing sugar" as used herein refers to a sugar that does not contain a hemi-acetal, for example a carbohydrate or sugar characterized by having a glycosidic bond formed between the reducing ends of the sugar units, and not between a reducing end of one sugar unit and a non-reducing end of the other sugar unit. In a further embodiment, the above-mentioned non-reducing sugar is trehalose or sucrose. In a further embodiment, the above-mentioned non-reducing sugar is sucrose. In an embodiment, the non-reducing sugar is in a concentration of about 0.1% to about 5% (w/w) in the pharmaceutical composition of the disclosure. In an embodiment, the non-reducing sugar is in a concentration of about 1% to about 3% (w/w). In a further embodiment, the non-reducing sugar is in a concentration of about 2% (w/w).

In an embodiment, the pharmaceutical composition of the present disclosure comprises a buffering agent, i.e. an agent that maintains the pH of the pharmaceutical composition near a chosen value. Examples of buffering agents include acetate buffers, succinate buffers, citrate buffers, phosphate buffers and histidine buffers. In an embodiment, the buffering agent is a histidine buffer. In an embodiment, the concentration of histidine in the pharmaceutical composition is about 0.01% to about 1%, for example about 0.05% to about 0.5% or about 0.1% to about 0.3%. In a further embodiment, the histidine sugar is in a concentration of about 0.15%.

In another embodiment, the amount of surfactant in the pharmaceutical composition of the present disclosure is about 0.0001% to about 10% (w/w). In a further embodiment, the amount of surfactant in the pharmaceutical composition of the present disclosure is about 0.001% to about 5%, 1% or 0.1% (w/w) or about 0.005% to about 0.05%. In yet a further embodiment, the amount of surfactant in the pharmaceutical composition of the present disclosure is about 0.01% (w/w).

In an embodiment, the pharmaceutical composition of the present disclosure comprises an oligosaccharide, for example a cyclic oligosaccharide such as a cyclodextrin. The term "cyclodextrin" as used herein refers to a family of cyclic oligosaccharides, comprising a macrocyclic ring of glucopyranoside subunits (5 or more) joined by α-1,4 glycosidic bonds. Examples of cyclodextrins include α-cyclodextrin, β-cyclodextrin and γ-cyclodextrin, which comprise 6, 7 and 8 glucopyranoside subunits, respectively, as well as analogs thereof (e.g., modified cyclodextrins). In an embodiment, the cyclodextrin is a β-cyclodextrin or a modified β-cyclodextrin. A modified β-cyclodextrin as used herein refers to a β-cyclodextrin molecule in which one or more of the hydroxyl groups of one or more of the sugar units may be modified, for example with an alkyl, alkenyl or alkynyl group, or with a substituted alkyl, alkenyl or alkynyl group. Therefore, in embodiments, the β-cyclodextrin may be unmodified or unsubstituted, or may be modified or substituted. As such, in a further embodiment, the β-cyclodextrin is a modified β-cyclodextrin. "Modified β-cyclodextrin" as used herein refers to a β-cyclodextrin that contains a modification at one or more hydroxyl groups of one or more sugar units of the β-cyclodextrin, i.e., a group or moiety that is attached to one or more hydroxyl groups of one or more sugar units of the β-cyclodextrin. As such, in embodiments, the modified β-cyclodextrin is an alkyl-, alkenyl-, alkynyl, substituted alkyl-, substituted alkenyl or substituted alkynyl-β-cyclodextrin (e.g., with a hydroxyl substitution). In embodiments, the alkyl, alkenyl or alkynyl groups are $(C_1-C_6)$alkyl, $(C_1-C_6)$alkenyl or $(C_1-C_6)$alkynyl groups. In a further embodiment, the modified β-cyclodextrin is a $(C_1-C_6)$alkyl β-cyclodextrin, in a further embodiment methyl-β-cyclodextrin (M-β-CD). In a further embodiment, the modified β-cyclodextrin is a hydroxy$(C_1-C_6)$alkyl β-cyclodextrin, in a further embodiment hydroxypropyl-β-cyclodextrin (HP-β-CD). In an embodiment, the cyclodextrin is present in the pharmaceutical composition at a concentration of about 2 to about 15% (w/v), in a further embodiment about 2 to about 12.5% (w/v), for example about 2 to about 10% (w/v), about 2.5 to about 15% (w/v), about 2.5 to about 12.5% (w/v), about 2.5 to about 10% (w/v), about 5 to about 15% (w/v), about 5 to about 12.5% (w/v), about 5 to about 10% (w/v), about 7.5 to about 12.5% (w/v), about 7.5 to about 10% (w/v), about 5, 7.5, 10, 12.5 or 15% (w/v), or about 10% (w/v).

In an embodiment, the pharmaceutical composition of the present disclosure has a pH of about 4.5 to about 6.5, for example about 5.0 to about 6.0. According to another embodiment, the pharmaceutical composition has a pH of about 5.0. According to a further embodiment, the pharmaceutical composition has a pH of about 5.5. According to another further embodiment, the pharmaceutical composition has a pH of about 6.0.

In an embodiment, the pharmaceutical composition of the present disclosure comprises a diluent, for example an aqueous solution. In a further embodiment, the pharmaceutical composition comprises (typically sterile) water.

The pharmaceutical composition of the present disclosure may further contain other diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, methionine and sulfhydryl-containing compounds such as thioalkanoic acid having 1 to 7 carbon atoms. Antioxidants include methionine, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate, sodium metaphosphate. Other components commonly added may also be contained, e.g., inorganic salts such as sodium chloride, potassium chloride, calcium chloride, sodium phosphate, potassium phosphate, sodium bicarbonate; and organic salts such as sodium citrate, potassium citrate, sodium acetate.

In an embodiment, the GHRH molecule, preferably trans-3-hexenoyl-GHRH$_{(1-44)}$-NH$_2$, or pharmaceutically acceptable salt thereof is administered at a daily dose of about 1 mg to about 8 mg. In a further embodiment, the GHRH molecule, preferably trans-3-hexenoyl-GHRH$_{(1-44)}$-NH$_2$, or pharmaceutically acceptable salt thereof is administered at a daily dose of about 1 mg to about 4 mg, about 1 mg to about 3 mg or about 1 mg to about 2 mg. In a further embodiment, the GHRH molecule, preferably trans-3-hexenoyl-GHRH$_{(1-44)}$-NH$_2$, or pharmaceutically acceptable salt thereof is administered at a daily dose of about 1, 1.1, 1.2, 1.3, 1.4, 1.5, 1.6, 1.7, 1.8, 1.9 or 2.0 mg.

In other aspects, the present disclosure provides a use of the above-mentioned GHRH molecule or composition for achieving one or more of the biological/therapeutic effects noted herein, e.g., for improving, reducing the progression of, stabilizing, reducing the severity of, preventing and/or treating the conditions, diseases or disorders noted herein, or for the preparation/manufacture of a medicament for improving, reducing the progression of, stabilizing, reducing the severity of, preventing and/or treating the conditions, diseases or disorders noted herein. In other aspects, the present disclosure provides the above-mentioned composition for use in improving, reducing the progression of, stabilizing, reducing the severity of, preventing and/or treating the conditions, diseases or disorders noted herein, or for the preparation/manufacture of a medicament for improving, reducing the progression of, reducing the severity of, preventing and/or treating the conditions, diseases or disorders noted herein.

The term "treatment" as used herein, is defined as the application or administration of a therapeutic agent to a subject, or application or administration of a therapeutic agent to an isolated tissue or cell line from a subject, who has a disorder, a disease, a symptom of disorder or disease, or a predisposition toward a disorder or disease, with the purpose to cure, heal, alleviate, delay, relieve, alter, remedy, ameliorate, improve or affect the disorder/disease, the symptoms of disorder/disease or the predisposition toward disorder/disease.

In an embodiment, the treatment is for a period of at least 3, 6, 9 or 12 months. In a further embodiment, the treatment is for a period of at least 12 months.

In embodiments, the GHRH molecule is for administration in an effective amount, e.g., a therapeutically effective amount or a prophylactically effective amount. A "therapeutically effective amount" refers to an amount effective, at dosages and for periods of time necessary, to achieve the desired therapeutic result, such as to effect the above-noted alterations and to reduce the progression of the above-noted conditions. A therapeutically effective amount of a GHRH molecule may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of onset or progression of the above-noted conditions. A prophylactically effective amount can be determined as described above for the therapeutically effective amount. For any particular subject, specific dosage regimens may be adjusted over time according to the individual need and the professional judgement of the person administering or supervising the administration of the compositions.

In accordance with another aspect of the disclosure, therapeutic compositions of the present disclosure, comprising a GH secretagogue, may be provided in containers, kits or packages (e.g. commercial packages) which further comprise instructions for its use to prevent or treat the conditions noted herein.

Accordingly, the disclosure further provides a kit or package comprising a GHRH molecule or the above-mentioned composition, optionally together with instructions to prevent or treat the conditions noted herein.

As used herein, the term "subject" or "patient" are taken to mean a warm-blooded animal such as a mammal, for example, a cat, a dog, a mouse, a guinea pig, a horse, a bovine cow, a sheep or a human. In an embodiment, the subject is a mammal. In a further embodiment, the subject is a human.

EXAMPLES

The present disclosure is illustrated in further detail by the following non-limiting examples.

Example 1: Materials and Methods

Participant Selection

Participants were recruited at the Massachusetts General Hospital (MGH, Boston, Mass.) and the National Institutes of Health (NIH, Bethesda, Md.). Potentially eligible participants were identified through referrals from local physicians, notices sent to participants enrolled in the Research Subject Volunteer Program at MGH, and the NIH cohort of patients with HIV and NAFLD. Sixty-one men and women with HIV-infection met eligibility criteria and participated in a baseline assessment.

Participants were eligible for the study if they were between 18-70 years of age and had confirmed HIV infection as well as hepatic steatosis as demonstrated by liver fat fraction of ≤5% on magnetic resonance spectroscopy (MRS). Participants with heavy alcohol use (>20 g daily for women or >30 g daily for men) were excluded, as were participants with hepatitis B, active hepatitis C, alpha-1 antitrypsin deficiency, Wilson's disease, hemochromatosis, or autoimmune hepatitis. Those with a history of hepatitis C were only eligible if they had been successfully treated, with resolution of hepatitis C at least one year prior to study entry and an undetectable HCV viral load at the screening visit. Participants with known cirrhosis, Stage 4 fibrosis on biopsy, or other severe chronic illness were also excluded. Participants with mild diabetes were eligible as long as hemoglobin A1c≤7%, anti-diabetic agents were stable for months, and they were not using insulin or thiazoledinediones. Participants were also required to have a stable antiviral regimen for months, stable use of any antihypertensive or lipid lowering medications for months, and, if applicable, stable use of vitamin E for ≥6 months prior to study entry. Participants using chronic systemic corticosteroids, methotrexate, amiodarone, tamoxifen, or GH were excluded, as were participants with any active malignancy. Women 50 y or older were required to have a negative mammogram within 1 year of the baseline visit, and men with history of prostate cancer were excluded. Participants with history of hypopituitarism or other conditions known to affect the GH axis were also ineligible. Other exclusionary labs for safety reasons were as follows: hemoglobin <11 g/dL, CD4+ count <100 cells/mm$^3$, HIV viral load >400 copies/mL, and prostate specific antigen <5 ng/mL.

Study Design

The study consisted of a 12-month, double-blind treatment phase during which participants were randomized in a 1:1 ratio receive to tesamorelin 2 mg daily or identical placebo, followed by a 6-month open label phase during which all participants receive tesamorelin. The pre-specified primary analysis, comparing changes over twelve months in tesamorelin vs. placebo treatment, is reported here. Randomization was stratified by site (NIH and MGH) and vitamin E use, defined as consistent use of ≥400 international units daily. The randomization list was prepared by the study statistician using a permuted block algorithm within each stratum with randomly varying block sizes. Tesamorelin was administered at the FDA-approved dose of 2 mg subcutaneously daily; participants were trained in reconstitution and self-injection at the baseline visit and administered the injections at home, returning used vials to assess compliance. IGF-1 Z-scores were monitored throughout the study by an independent endocrinologist at MGH otherwise unaffiliated with the study. A pre-specified threshold of IGF-1 Z-score of ≥3 was included in the protocol as a trigger to decrease tesamorelin dose to 1 mg, along with a dummy dose-reduction in the placebo group, but this was not required for any patient during the double-blind phase of the study.

All subjects received nutritional counseling from clinical research nutritionists at baseline, six and 12 months. Visits were conducted in the fasting state. The screening visit included history and physical examination, laboratory investigations for eligibility, MRS and magnetic resonance imaging (MRI), with the latter used to assess cross-sectional area of visceral adipose tissue (VAT) at the L4 vertebra. The MRI/MRS, HbA1c, CD4+ count, and HIV viral load from the screening visit were used as the baseline measures. The baseline assessment included liver biopsy; whole body dual energy x-ray absorptiometry (DXA); fasting assessment of liver function tests, lipids, serum inflammatory markers, IGF-1, and HbA1c; and bionutrition assessment including 4-day food record, Modifiable Activity Questionnaire (Kriska A M, et al. *Diabetes Care* 1990; 13:401-11), and anthropometric measures performed in triplicate. Baseline assessments were repeated at 12 months along with repeat MRI/MRS, HbA1c, and immunologic parameters. An interim MRI/MRS was performed at the 6-month visit.

Outcome Measures

The primary outcome was HFF as measured using $^1$H MRS, performed in the morning following an 8-hour fast. Fat fraction was calculated as the area under the spectroscopic lipid peak divided by the total area under the water and lipid peaks. Image acquisition followed a standard protocol at MGH and NIH. Liver fat content was quantified using jMRUI semi-automated software at NIH and automated LC-Model software at MGH. NIH scans were re-read at MGH using LC-Model, and the correlation between measurements was 0.97, equivalent to the correlation between two scans performed on the same machine before and after repositioning and analyzed using LC-Model (Bredella M A, et al. *J Comput Assist Tomogr* 2010; 34:372-6). The diagnostic accuracy of MRS for liver steatosis has an area under the receiver operating characteristic curve of 0.94 (95% CI 0.88-1.0) compared to assessment of liver biopsy by an experienced pathologist (Georgoff P, et al. *AJR Am J Roentgenol* 2012; 199:2-7). Subjects were eligible if HFF was ≥5%.

Histological scoring was performed by a blinded central pathologist (DEK) for all liver biopsy samples using the NAS CRN scoring system (Kleiner D E, et al. *Hepatology* 2005; 41:1313-21). The sum of grades for steatosis (grades 0-3), hepatocellular ballooning (grades 0-2), and lobular inflammation (0-3) comprise the NAS, and fibrosis is independently staged between 0-4 (Kleiner D E, et al. *Hepatology* 2005; 41:1313-21). Presence or absence of steatohepatitis was determined by histological review (DEK). Progression of fibrosis was considered any increase in fibrosis stage between baseline and 12 months. Cross-sectional MRI of the abdomen at the L4 vertebra was read centrally and used to quantify VAT and subcutaneous adipose tissue (SAT) areas.

Participants at MGH also underwent a euglycemic hyperinsulinemic clamp procedure to assess insulin sensitivity. After a 14-hour overnight fast, a low-dose (insulin 20 mU/m$^2$/min) clamp for 2 hours was followed by a high-dose (insulin 80 mU/m$^2$/min) clamp for 2 hours as previously described (Braun L R, et al. Effects of Pitavastatin on Insulin Sensitivity and Liver Fat: A Randomized Clinical Trial. *J Clin Endocrinol Metab* 2018; 103:4176-86). Insulin stimulated glucose disposal (M) were calculated during the last 20 minutes of low-dose and high-dose clamp using the DeFronzo method (DeFronzo R A, Tobin J D, Andres R. *Am J Physiol* 1979; 237:E214-23) as the primary indices of hepatic and whole-body insulin sensitivity, respectively.

Laboratory analyses were conducted using standard methodologies. Clinical labs were measured at the NIH Clinical Laboratory and, for MGH, at LabCorp and Quest. IGF-1 was measured centrally at Quest Laboratories. C-reactive protein was measured using electrochemiluminescense (Meso Scale Discovery, Rockville, Md.), and adiponectin was measured using ELISA (R&D Systems, Minneapolis, Minn.).

Statistical Analysis

The pre-specified primary endpoint was change in HFF between baseline and 12 months. Secondary endpoints included change in liver histology, ALT, lipids, measures of glucose metabolism, and markers of systemic inflammation. A sample size of 60 was chosen based on 80% power to detect a treatment difference of 0.85 standard deviation change in hepatic fat fraction over 12 months, assuming a discontinuation rate of 25%, i.e., 45 evaluable patients, at a two-sided alpha of 0.05. After one patient at the MGH site discontinued at the conclusion of the baseline visit, IRB permission was obtained to enroll a 61$^{st}$ participant.

Per the pre-specified analysis plan, change in HFF was assessed by random intercept mixed effects modeling using restricted maximum likelihood to assess the effect estimate for the time×randomization interaction. All available data were used in the analysis, which was based on intention to treat. The same analysis was used for other endpoints measured at multiple timepoints during the double-blind period, including VAT, SAT, ALT, BMI, and glucose. For secondary endpoints measured at only baseline and 12-months, a paired t-test was performed using all available data. Data are presented as mean±standard deviation or, for categorical variables, number and percent. Between group comparisons at baseline were assessed using Student's t-test for continuous variables and Pearson's Chi Square statistic for categorical variables. Pearson's correlation coefficient was used to assess relationships between continuous variables. Two data points one baseline ALT value and one baseline CRP value were excluded due to being more than 5 standard deviations above the sample mean. A two-sided alpha of 0.05 was the pre-defined threshold for statistical significance. Study data were collected and managed using Research Electronic Data Capture (REDCap) tools hosted at Partners HealthCare (Harris P A, et al. *J Biomed Inform* 2009; 42:377-81). Sensitivity analyses were performed utilizing multiple imputation of missing data with 100 iterations, discarding the first 10. All data analysis was overseen by the study statistician (HL).

Example 2: Results

Patients' Characteristics, Adherence

Of 143 total participants screened, 61 entered the randomized treatment portion of the trial. Fifteen participants were recruited at NIH and 46 at MGH. Participant flow and reasons for patient exclusion are shown in FIG. 1. Four participants in the tesamorelin group and two in the placebo group discontinued before any follow-up imaging, as shown in FIG. 1. Five participants in the tesamorelin group and two in the placebo group discontinued after obtaining follow-up imaging that was used in the primary analysis. The overall discontinuation rate was not significantly different between groups, P=0.12.

Clinical characteristics (Table 1) and measures of body composition and metabolism (FIG. 2) were similar between groups at baseline (FIG. 2). At baseline, 33% of the cohort had a histologic diagnosis of NASH. Forty-three percent of the cohort had fibrosis Stage 1 or higher; per protocol, none had Stage 4 fibrosis at baseline. These rates were similar in the treatment groups (Table 1). ART regimen was similar between groups (Table 1).

TABLE 1

Baseline Demographics and Clinical Characteristics

|  | Tesamorelin (n = 31) | Placebo (n = 30) |
|---|---|---|
| Sex (N [%] Male) | 24 [77.4%] | 24 [80.0%] |
| Age (y) | 52 ± 8 | 54 ± 7 |
|  | 51 [47, 56] | 55 [49, 60] |
| Race (N [%]) |  |  |
| White | 21 [67.7%] | 19 [63.3%] |
| Black | 8 [25.8%] | 10 [33.3%] |
| Other | 2 [6.5%] | 1 [3.3%] |
| Ethnicity (N [%] Hispanic) | 6 [19.4%] | 3 [10.0%] |
| Smoking Status (N [%]) |  |  |
| Ever Smoker | 15 [53.6%] | 12 [52.2%] |
| Current Smoker* | 4 [12.9%] | 7 [23.3%] |
| Alcohol Use (drinks/week) | 0.3 ± 1.3 | 0.9 ± 2.0 |
| Duration of HIV Infection | 16 ± 9 | 18 ± 8 |
|  | 16 [10, 22] | 20 [11, 24] |
| Current Antiretroviral Use (N [%]) |  |  |
| NRTI | 27 [87.1%] | 29 [96.7%] |
| PI | 9 [29.0%] | 6 [20.0%] |

TABLE 1-continued

Baseline Demographics and Clinical Characteristics

|  | Tesamorelin (n = 31) | Placebo (n = 30) |
|---|---|---|
| NNRTI | 12 [38.7%] | 11 [36.7%] |
| Integrase Inhibitors | 21 [67.7%] | 18 [60%] |
| Entry Inhibitor | 1 [3.2%] | 0 [0%] |
| Type 2 Diabetes (N [%]) | 4 [12.9%] | 4 [13.3%] |
| Current use of anti-diabetics | 3 [9.7%] | 3 [10.0%] |
| Current metformin use | 3 [9.7%] | 2 [6.7%] |
| Current Lipid Lowering Medications (N [%]) | 13 [41.9%] | 15 [50.0%] |
| Current statin use | 10 [32.3%] | 14 [46.7%] |
| Current Vitamin E Use (N [%]) | 2 [6.5%] | 1 [3.3%] |
| Hepatic Fat (%) | 14.7 ± 9.0 | 12.9 ± 7.7 |
| NASH (N [%]) | 10 [34.5%] | 9 [31.0%] |
| Fibrosis (N [%]) | 14 [48.3%] | 11 [37.9%] |

There were no statistically significant differences between groups at baseline for any of the variables shown above. Continuous variables are presented as mean ± standard deviation.
*Current smokers are also represented in the "Ever Smoker" category.
**Vitamin E use defined as regular use of ≥ 400 international units daily.
Abbreviations:
g, grams;
HIV, human immunodeficiency virus;
kcal, kilocalories;
NASH, nonalcoholic steatohepatitis,
NRTI, nucleoside reverse transcriptase inhibitor;
PI, protease inhibitor;
NNRTI nonnucleoside reverse transcriptase inhibitor.

Adherence to daily injections by count of returned empty vials was similar between treatment groups: 87±16% for placebo and 80±15% for tesamorelin (P=0.11). Change in IGF-1 values, shown in FIG. 2, demonstrate the expected effect of tesamorelin to increase IGF-1, with an effect size of 117 ng/mL (95% CI [76, 157], P<0.0001). No subjects had IGF-1 Z-scores over the pre-specified dose-reduction threshold (Z-score >3), but one subject received a dose reduction to 1 mg for symptoms potentially related to growth hormone. This subject self-discontinued from the study soon after the dose reduction.

Hepatic Fat Fraction, Liver Histology, and Markers of Inflammation

Table 2A shows the hepatic fat fraction (HFF) at baseline and at the end of the 1-year treatment in tesamorelin- and placebo-treated subjects who completed the study. Table 2B shows the NASH score, steatosis score, hepatocellular ballooning score and lobular inflammation score at baseline and at the end of the 1-year treatment in tesamorelin- and placebo-treated subjects who completed the study. Table 2C shows the fibrosis stage at baseline and at the end of the 1-year treatment in tesamorelin- and placebo-treated subjects who completed the study.

TABLE 2A

| | | Hepatic Fat Fraction (HFF) | | | |
|---|---|---|---|---|---|
| Patient No. | Treatment | Baseline | Year 1 | Change (absolute) | Change (relative) |
| 2 | Tesamorelin | 8.10 | 2.94 | −5.16 | −64% |
| 3 | Tesamorelin | 11.88 | 3.85 | −8.03 | −68% |
| 4 | Tesamorelin | 10.60 | 7.87 | −2.73 | −26% |
| 7 | Tesamorelin | 16.97 | 2.87 | −14.1 | −83% |
| 12 | Tesamorelin | 5.38 | 1.78 | −3.6 | −67% |
| 13 | Tesamorelin | 23.96 | 23.08 | −0.88 | −4% |
| 18 | Tesamorelin | 5.36 | 1.59 | −3.77 | −70% |
| 20 | Tesamorelin | 9.09 | 10.22 | 1.13 | 12% |
| 24 | Tesamorelin | 33.19 | 17.40 | −15.79 | −48% |
| 26 | Tesamorelin | 15.03 | 2.14 | −12.89 | −86% |
| 28 | Tesamorelin | 14.26 | 10.22 | −4.04 | −28% |
| 29 | Tesamorelin | 19.91 | 19.89 | −0.02 | 0% |

TABLE 2A-continued

| | | Hepatic Fat Fraction (HFF) | | | |
|---|---|---|---|---|---|
| Patient No. | Treatment | Baseline | Year 1 | Change (absolute) | Change (relative) |
| 31 | Tesamorelin | 11.67 | 5.97 | −5.7 | −49% |
| 34 | Tesamorelin | 7.50 | 5.42 | −2.1 | −28% |
| 36 | Tesamorelin | 9.10 | 23.93 | 14.83 | 163% |
| 37 | Tesamorelin | 13.02 | 8.86 | −4.16 | −32% |
| 50 | Tesamorelin | 24 | 20 | −4 | −17% |
| 51 | Tesamorelin | 5 | 1.4 | −3.6 | −72% |
| 53 | Tesamorelin | 17 | 9 | −8 | −47% |
| 55 | Tesamorelin | 33.33 | 21 | −12.33 | −37% |
| Average Tesamorelin | | 14.72 | 9.97 | −4.75 | −32% |
| Median Tesamorelin | | 12.75 | 8.37 | −4.02 | −42% |
| 5 | Placebo | 5.27 | 8.72 | 3.45 | 65% |
| 6 | Placebo | 11.54 | 7.73 | −3.81 | −33% |
| 8 | Placebo | 6.85 | 9.57 | 2.72 | 40% |
| 10 | Placebo | 45.38 | 39.18 | −6.2 | −14% |
| 11 | Placebo | 28.45 | 24.43 | −4.02 | −14% |
| 15 | Placebo | 4.98 | 1.09 | −3.89 | −78% |
| 16 | Placebo | 14.27 | 21.68 | 7.41 | 52% |
| 17 | Placebo | 11.64 | 12.63 | 0.99 | 9% |
| 19 | Placebo | 10.00 | 10.13 | 0.13 | 1% |
| 21 | Placebo | 6.24 | 14.14 | 7.9 | 127% |
| 23 | Placebo | 18.97 | 25.46 | 6.49 | 34% |
| 27 | Placebo | 5.50 | 5.09 | −0.41 | −7% |
| 30 | Placebo | 11.43 | 8.90 | −2.53 | −22% |
| 32 | Placebo | 13.94 | 12.37 | −1.57 | −11% |
| 33 | Placebo | 25.94 | 20.51 | −5.43 | −21% |
| 35 | Placebo | 7.42 | 6.04 | −1.38 | −19% |
| 38 | Placebo | 17.85 | 21.65 | 3.8 | 21% |
| 39 | Placebo | 11.73 | 13.20 | 1.47 | 13% |
| 42 | Placebo | 5.90 | 9.29 | 3.39 | 57% |
| 44 | Placebo | 13.27 | 15.44 | 2.17 | 16% |
| 47 | Placebo | 16.6 | 16.1 | −0.5 | −3% |
| 48 | Placebo | 30 | 33 | 3 | 10% |
| 52 | Placebo | 16 | 11 | −5 | −31% |
| 54 | Placebo | 14.63 | 10.3 | −4.6 | −31% |
| 60 | Placebo | 10 | 5.55 | −4.45 | −45% |
| Average Placebo | | 14.55 | 14.53 | −0.035 | 5% |
| Median Placebo | | 11.73 | 12.37 | −0.41 | −3% |

TABLE 2B

| | | NASH score | | Steatosis | | Lobular inflammation | | Ballooning | |
|---|---|---|---|---|---|---|---|---|---|
| Patient No. | Treatment | Base | Year 1 | Base | Year 1 | Base | Year 1 | Base | Year 1 |
| 2 | Tesa | 2 | 1 | 1 | 1 | 1 | 0 | 0 | 0 |
| 3 | Tesa | 3 | 4 | 1 | 1 | 1 | 2 | 1 | 1 |
| 4 | Tesa | 2 | 2 | 1 | 1 | 1 | 1 | 0 | 0 |
| 12 | Tesa | 2 | 1 | 1 | 0 | 1 | 1 | 0 | 0 |
| 13 | Tesa | 3 | 1 | 2 | 1 | 1 | 0 | 0 | 0 |
| 18 | Tesa | 1 | 1 | 0 | 0 | 1 | 1 | 0 | 0 |
| 20 | Tesa | 3 | 2 | 1 | 1 | 1 | 1 | 1 | 0 |
| 24 | Tesa | 3 | 3 | 2 | 2 | 1 | 1 | 0 | 0 |
| 28 | Tesa | 2 | 1 | 1 | 1 | 1 | 0 | 0 | 0 |
| 29 | Tesa | 2 | 4 | 1 | 2 | 1 | 1 | 0 | 1 |
| 31 | Tesa | 2 | 2 | 1 | 1 | 1 | 1 | 0 | 0 |
| 34 | Tesa | 1 | 1 | 0 | 0 | 1 | 1 | 0 | 0 |
| 36 | Tesa | 1 | 4 | 1 | 3 | 0 | 1 | 0 | 0 |
| 37 | Tesa | 0 | 1 | 0 | 1 | 0 | 0 | 0 | 0 |
| 50 | Tesa | 7 | 7 | 2 | 3 | 3 | 2 | 2 | 2 |
| 51 | Tesa | 2 | 1 | 1 | 0 | 1 | 1 | 0 | 0 |
| 53 | Tesa | 3 | 3 | 1 | 1 | 1 | 1 | 1 | 1 |
| 55 | Tesa | 7 | 4 | 2 | 2 | 3 | 1 | 2 | 1 |
| 5 | Placebo | 2 | 2 | 1 | 1 | 1 | 1 | 0 | 0 |
| 6 | Placebo | 2 | 2 | 1 | 1 | 1 | 1 | 0 | 0 |
| 8 | Placebo | 3 | 2 | 1 | 1 | 2 | 1 | 0 | 0 |
| 10 | Placebo | 7 | 7 | 3 | 3 | 2 | 2 | 2 | 2 |
| 11 | Placebo | 3 | 4 | 2 | 2 | 1 | 1 | 0 | 1 |
| 15 | Placebo | 1 | 1 | 0 | 0 | 1 | 1 | 0 | 0 |
| 16 | Placebo | 2 | 2 | 1 | 1 | 1 | 1 | 0 | 0 |
| 17 | Placebo | 2 | 2 | 1 | 1 | 1 | 1 | 0 | 0 |
| 19 | Placebo | 4 | 2 | 1 | 1 | 1 | 1 | 2 | 0 |
| 21 | Placebo | 4 | 5 | 3 | 2 | 1 | 2 | 0 | 1 |
| 23 | Placebo | 3 | 2 | 2 | 1 | 1 | 1 | 0 | 0 |
| 27 | Placebo | 2 | 1 | 1 | 0 | 1 | 1 | 0 | 0 |
| 30 | Placebo | 2 | 2 | 1 | 1 | 1 | 1 | 0 | 0 |
| 32 | Placebo | 1 | 2 | 0 | 1 | 1 | 1 | 0 | 0 |
| 33 | Placebo | 4 | 3 | 2 | 2 | 1 | 1 | 1 | 0 |
| 35 | Placebo | 1 | 1 | 0 | 1 | 1 | 0 | 0 | 0 |
| 38 | Placebo | 4 | 7 | 1 | 2 | 2 | 3 | 1 | 2 |
| 42 | Placebo | 1 | 2 | 0 | 1 | 1 | 1 | 0 | 0 |
| 44 | Placebo | 2 | 3 | 1 | 1 | 1 | 2 | 0 | 0 |
| 47 | Placebo | 7 | 6 | 3 | 3 | 2 | 1 | 2 | 2 |
| 48 | Placebo | 5 | 6 | 3 | 3 | 1 | 2 | 1 | 1 |
| 52 | Placebo | 2 | 3 | 1 | 1 | 1 | 1 | 0 | 1 |
| 56 | Placebo | 2 | 2 | 1 | 1 | 1 | 1 | 0 | 0 |
| 60 | Placebo | 2 | 2 | 1 | 1 | 1 | 1 | 0 | 0 |

TABLE 2C

| Patient No. | Treatment | Fibrosis stage Baseline | Year 1 |
|---|---|---|---|
| 2 | Tesamorelin | 0 | 0 |
| 3 | Tesamorelin | 3 | 4 |
| 4 | Tesamorelin | 0 | 0 |
| 12 | Tesamorelin | 0 | 0 |
| 13 | Tesamorelin | 0 | 0 |
| 18 | Tesamorelin | 1B | 0 |
| 20 | Tesamorelin | 1A | 1A |
| 24 | Tesamorelin | 0 | 0 |
| 28 | Tesamorelin | 0 | 0 |
| 29 | Tesamorelin | 10 | 10 |
| 31 | Tesamorelin | 0 | 0 |
| 34 | Tesamorelin | 2 | 2 |
| 36 | Tesamorelin | 0 | 0 |
| 37 | Tesamorelin | 0 | 0 |
| 50 | Tesamorelin | 3 | 3 |
| 51 | Tesamorelin | 0 | 0 |
| 53 | Tesamorelin | 2 | 3 |
| 55 | Tesamorelin | 2 | 1A |
| 5 | Placebo | 10 | 0 |
| 6 | Placebo | 0 | 0 |
| 8 | Placebo | 3 | 10 |
| 10 | Placebo | 2 | 2 |
| 11 | Placebo | 0 | 2 |
| 15 | Placebo | 0 | 0 |
| 16 | Placebo | 0 | 0 |
| 17 | Placebo | 0 | 0 |
| 19 | Placebo | 2 | 1A |
| 21 | Placebo | 2 | 3 |
| 23 | Placebo | 0 | 0 |
| 27 | Placebo | 0 | 0 |
| 30 | Placebo | 0 | 1A |
| 32 | Placebo | 1A | 1B |
| 33 | Placebo | 0 | 0 |
| 35 | Placebo | 0 | 0 |
| 38 | Placebo | 2 | 3 |
| 42 | Placebo | 0 | 10 |
| 44 | Placebo | 0 | 10 |
| 47 | Placebo | 3 | 3 |
| 48 | Placebo | 1B | 2 |
| 52 | Placebo | 0 | 1B |
| 56 | Placebo | 0 | 0 |
| 60 | Placebo | 0 | 0 |

Figure 3A:
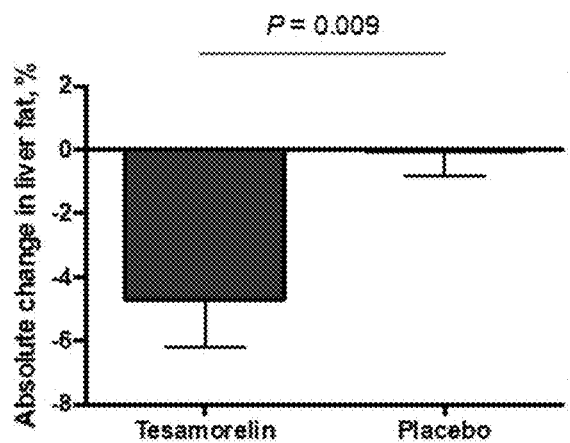
FIGS. 3A and 3B are graphs depicting the change in absolute (FIG. 3A) and relative (FIG. 3B) liver fat content between baseline and 12 months, with p-values shown for t-test comparing change between groups.
Figure 3B:
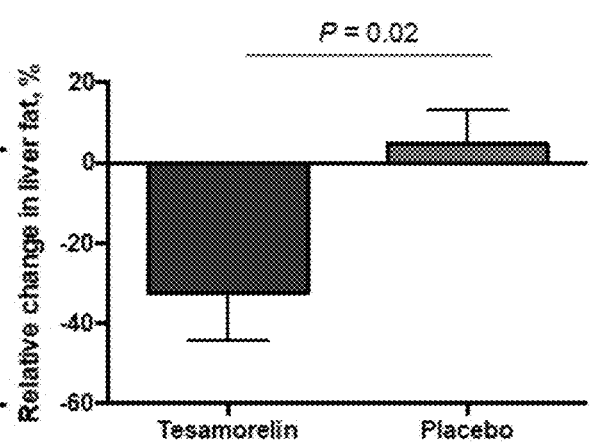
Figure 3C:
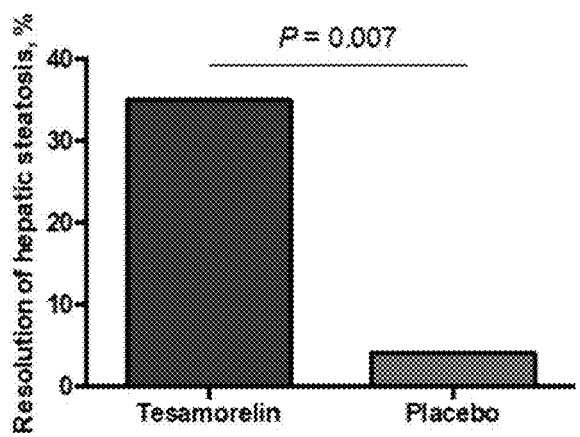
FIG. 3C is a graph depicting the percent resolution of steatosis, defined as 12-month hepatic fat fraction <5%, with P-value for Pearson Chi-Square.

Tesamorelin significantly reduced HFF compared to placebo (effect size −4.1% (95% CI −7.5, −0.7), P=0.02) compared to placebo. The change between baseline and 12 months, shown in FIG. 3A, corresponded to a −37% (95% CI −67, −7) relative change in liver fat (FIG. 3B). In the tesamorelin group, 35% of individuals had a reduction in HFF to <5%, whereas this occurred in 4% of individuals in the placebo group (FIG. 3C, P=0.007 for comparison). Also, tesamorelin was effective at reducing HFF in the most afflicted subjects (i.e. subjects having the most elevated baseline HFF, e.g., ≥15%), with some patients showing absolute reduction of HFF of more than 10%: from 16.97 to 2.87 for patient no. 7; from 33.19 to 17.4 for patient no. 24; from 15.03 to 2.14 for patient no. 26; and from 33.3 to 21 for patient no. 55 (Table 2A).

Figure 4A:
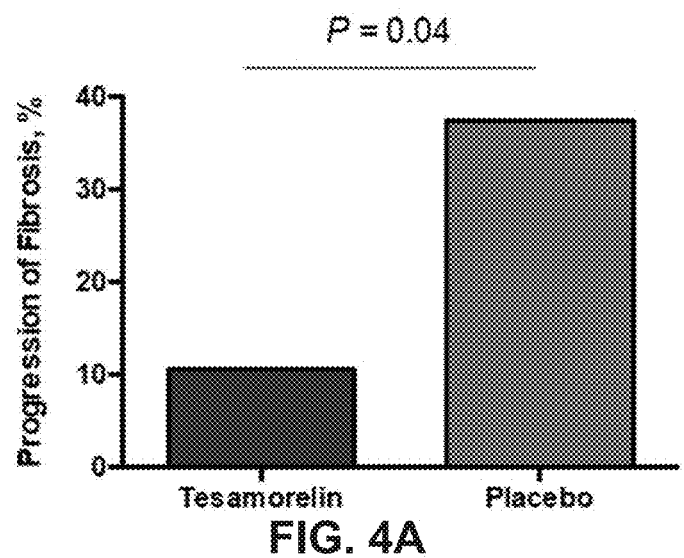
FIG. 4A is a graph depicting the percentage of patients with progression of fibrosis at 12 months, with P-value for Pearson Chi-Square.
Figure 4B:
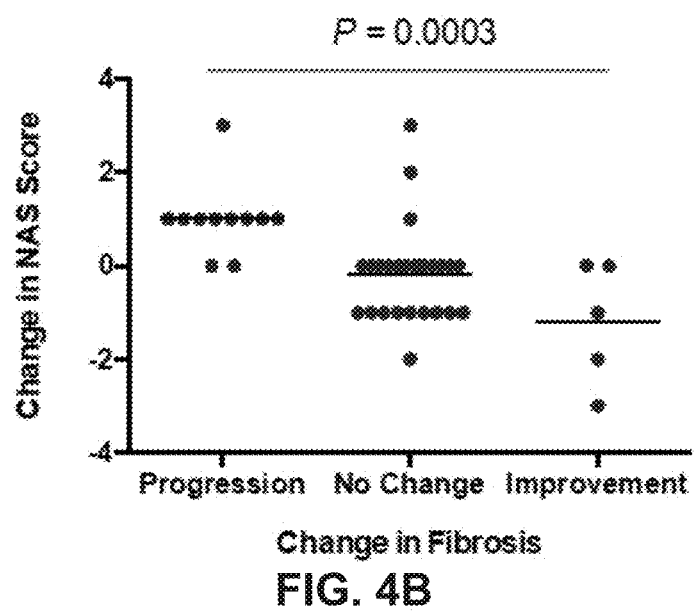
FIG. 4B is a graph depicting the relationship between change in fibrosis and change in NAS score at 12 months, with P-value for ANOVA.

Among the entire cohort, tesamorelin prevented the progression of fibrosis during the treatment period, with 2 individuals showing progression in the tesamorelin group versus 9 in the placebo group (P=0.04) (FIG. 4A). Changes in fibrosis during the study were positively associated with changes in NAS score (p-value for ANOVA=0.0003, FIG. 4B). Among the entire cohort, tesamorelin did not significantly change NAS score relative to placebo (effect size −0.3, 95% CI −1.0, 0.5). However, among individuals randomized to tesamorelin, those with higher baseline NAS scores had greater reductions in their scores during treatment (r=−0.48, P=0.04), whereas a similar relationship was not observed in the placebo group (r=−0.14, P=0.52). Notably, the NAS score of patient No. 55 treated with tesamorelin was reduced from 7 to 4, which was associated with an improvement of fibrosis (from stage 2 to 1A) (Tables 2B and 2C). Similarly, in the tesamorelin-treated cohort, changes in NAS score during the treatment period were positively associated with changes in HFF (r=0.51, P=0.03), whereas a similar relationship was not seen in placebo-treated patients (r=0.14, P=0.52).

Figure 3D:
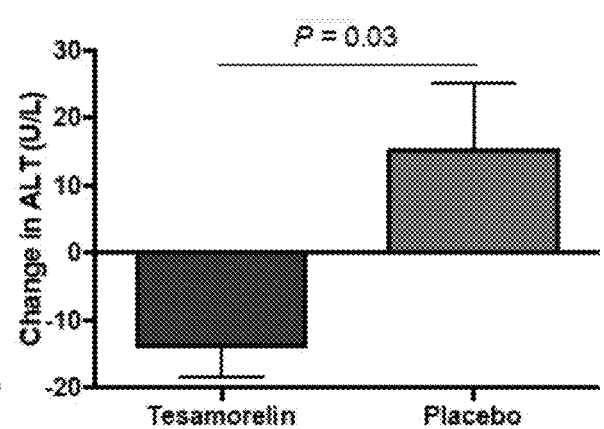
FIG. 3D is a graph depicting the change in alanine aminotransferase (ALT) between baseline and 12 months for those with ALT 30 U/L at baseline, with p-value for t-test comparing change between groups.

Relative to placebo, tesamorelin did not significantly reduce ALT or GGT over the treatment period, although both effect sizes suggest a modest reduction (FIG. 2). Restricting the cohort to those with elevated ALT (>30 U/L) at baseline, tesamorelin did significantly decrease ALT after 12 months (effect size −29 U/L [95% CI −3, −55], P=0.03, FIG. 3D) relative to placebo. Tesamorelin reduced CRP (FIG. 2) relative to placebo but did not have any effect on adiponectin.

Lipid and Glucose Metabolism and Body Composition

No effect of tesamorelin on low-density lipoprotein cholesterol (LDL-C), high-density lipoprotein cholesterol (HDL-C), or triglycerides (FIG. 2) was seen in the present study. Tesamorelin did not significantly affect fasting glucose or hemoglobin A1c during the treatment period (FIG. 2). In the subset of patients who underwent euglycemic hyperinsulinemic clamp, tesamorelin did not affect the glucose infusion rate required during the low-dose clamp (treatment effect for low-dose M 0.0 mg/kg/min [95% CI −1.1, 1.1], P=0.996) nor the insulin stimulated glucose uptake during the high-dose clamp (treatment effect for high-dose M −0.9 mg/kg/min [95% CI −2.4, 0.7].

Table 3 shows the visceral adiposity at baseline and at the end of the 1-year treatment in tesamorelin- and placebo-treated subjects who completed the study.

TABLE 3

| Patient No. | Treatment | Visceral adiposity (cm²) | | |
|---|---|---|---|---|
| | | Baseline | Year 1 | Relative change |
| 2 | Tesamorelin | 130.79 | 107.84 | −18% |
| 3 | Tesamorelin | 218.12 | 242.96 | 11% |
| 4 | Tesamorelin | 96.30 | 80.86 | −16% |
| 7 | Tesamorelin | 171.49 | 146.32 | −15% |
| 12 | Tesamorelin | 176.60 | 174.63 | −1% |
| 13 | Tesamorelin | 250.91 | 244.77 | −2% |
| 18 | Tesamorelin | 151.59 | 141.88 | −6% |
| 20 | Tesamorelin | 159.08 | 109.01 | −31% |
| 24 | Tesamorelin | 238.57 | 240.79 | 1% |
| 26 | Tesamorelin | 203.14 | 28.55 | −86% |
| 28 | Tesamorelin | 332.87 | 346.80 | 4% |
| 29 | Tesamorelin | 329.31 | 424.63 | 29% |
| 31 | Tesamorelin | 191.63 | 98.62 | −49% |
| 34 | Tesamorelin | 251.99 | 250.21 | −1% |
| 36 | Tesamorelin | 329.89 | 290.85 | −12% |
| 37 | Tesamorelin | 131.36 | 322.94 | 146% |
| 50 | Tesamorelin | 300.71 | 240.42 | −20% |
| 51 | Tesamorelin | 265.39 | 133.00 | −50% |
| 53 | Tesamorelin | 446.64 | 352.00 | −21% |
| 55 | Tesamorelin | 364.66 | 335.48 | −8% |
| Average Tesamorelin | | 237.05 | 215.63 | −7% |
| Median Tesamorelin | | 228.35 | 221.02 | −10% |
| 5 | Placebo | 248.72 | 338.55 | 36% |
| 6 | Placebo | 122.45 | 132.92 | 9% |
| 8 | Placebo | 147.46 | 181.43 | 23% |
| 10 | Placebo | 394.51 | 346.46 | −12% |
| 11 | Placebo | 252.69 | 257.89 | 2% |
| 15 | Placebo | 136.05 | 176.25 | 30% |
| 16 | Placebo | 311.93 | 335.45 | 8% |
| 17 | Placebo | 220.00 | 225.39 | 2% |

TABLE 3-continued

| | | Visceral adiposity (cm$^2$) | | |
|---|---|---|---|---|
| Patient No. | Treatment | Baseline | Year 1 | Relative change |
| 19 | Placebo | 286.46 | 272.48 | −5% |
| 21 | Placebo | 166.76 | 169.40 | 2% |
| 23 | Placebo | 193.37 | 233.44 | 21% |
| 27 | Placebo | 86.57 | 94.40 | 9% |
| 30 | Placebo | 245.57 | 317.52 | 29% |
| 32 | Placebo | 339.45 | 402.50 | 19% |
| 33 | Placebo | 291.68 | 272.24 | −7% |
| 35 | Placebo | 116.14 | 134.17 | 16% |
| 38 | Placebo | 230.47 | 141.44 | −39% |
| 39 | Placebo | 243.94 | 304.42 | 25% |
| 42 | Placebo | 190.16 | 231.52 | 22% |
| 44 | Placebo | 493.68 | 562.60 | 14% |
| 47 | Placebo | 259.48 | 238.15 | −8% |
| 48 | Placebo | 476.77 | 448.03 | −6% |
| 52 | Placebo | 357.75 | 356.78 | 0% |
| 54 | Placebo | 138.49 | 141.17 | 2% |
| 56 | Placebo | 235.52 | 241.11 | 2% |
| 60 | Placebo | 122.65 | 118.99 | −3% |
| Average Placebo | | 242.64 | 256.72 | 7% |
| Median Placebo | | 239.73 | 239.63 | 5% |

Tesamorelin significantly reduced VAT area relative to placebo, with no effect on SAT area (FIG. 2). Tesamorelin modestly increased lean body mass by DXA, with no significant effect on total body fat mass (FIG. 2). Body mass index and waist circumference did not change.

Nutrition and Physical Activity

As assessed by Modifiable Activity Questionnaire, there were no significant changes in daily caloric and macronutrient intake by four-day food record, self-reported alcoholic drinks per week, and hours of activity per week between baseline and 12-months.

Sensitivity Analyses

Sensitivity analyses for the primary endpoint were performed using multiple imputation for missing data. This data confirmed the primary results, with estimated effect size of −3.8% (95% coverage −5.4, −2.2) reduction in HFF.

Adverse Effects

Adverse events by study group are shown in Table 4. A limited number of serious adverse events (SAEs) were seen, which did not differ by treatment arm. None were judged as related to study drug. In the placebo group, two individuals had SAEs and were hospitalized: one following a suicide attempt, and one following a hematoma post liver biopsy. In the tesamorelin group, four individuals had SAEs and were hospitalized: one with a history of stroke with transient hemiplegia for which a cause was not found, one due to suicidal ideation, one for urosepsis, and one for pneumonia and separately for influenza.

One individual in the placebo group and four in the tesamorelin group had events that met a priori protocol criteria for investigator discontinuation (P=0.17, including two discontinuations for hyperglycemia (2-week and 6-month visits) in the tesamorelin group. One had known diabetes at baseline. Other reasons for discontinuation are outlined in FIG. 1.

TABLE 4

| Adverse Events | | | |
|---|---|---|---|
| | Tesamorelin | Placebo | P-value for comparison* |
| Any adverse event | 29 | 29 | 0.57 |
| Serious adverse event | 4 | 2 | 0.41 |
| Event meeting criteria for discontinuation by investigator | 4 | 1 | 0.17 |
| Hyperglycemia | 12 | 11 | |
| Arthralgia | 3 | 3 | |
| Myalgia | 2 | 0 | |
| Paresthesia | 2 | 2 | |
| Injection site bruising | 11 | 11 | |
| Injection site erythema | 3 | 0 | |
| Injection site stinging | 4 | 1 | |
| Other injection site complaints | 10 | 1 | |
| URI | 5 | 5 | |
| Other infection | 7 | 12 | |
| Other | 25 | 24 | |

Numbers refer to numbers of patients with events.
*P-value for comparison of numbers of events by group by Pearson Chi-Square. The study was not powered to detect differences in adverse events, and p-values are shown only for aggregate events.

Example 3: Gene Set Enrichment Analysis (GSEA) on Samples from Tesamorelin and Placebo Groups Gene Set Enrichment Analysis (GSEA) (Subramanian, Tamayo, et al., 2005, PNAS 102, 15545-15550; Mootha, Lindgren, et al., 2003, *Nat Genet* 34, 267-273) using Hallmark and curated gene sets were performed on RNAseq data generated liver tissues from Tesamorelin and Placebo groups to determine whether Tesamorelin administration is associated with the overexpression and/or downregulation of specific gene sets or pathways. Paired liver biopsy specimens from the study (tesamorelin, n=19; placebo, n=24) were utilized after preparation with RNAlater™. Change in gene expression was successfully evaluated in 18 patients in the tesamorelin group and 21 in the placebo group. An automated variant of the Illumina TruSeq™ Stranded mRNA Sample Preparation Kit was used to deliver 50M reads aligned in pairs. Each run is a 101 bp paired-end with an eight-base index barcode read. Data was analyzed using the Broad Picard Pipeline, which includes de-multiplexing and data aggregation. Alignment is completed using the STAR alignment algorithm. TruSeq Strand Specific Large Insert RNA Sequencing includes plating, poly-A selection and strand specific cDNA synthesis, library preparation (450-550 bp insert size), sequencing (101 bp paired reads), sample identification QC check (when Sample Qualification of a matching DNA sample is chosen). The product provides library construction using a strand specific Illumina TruSeq™ Protocol and sequence coverage to 50M Paired reads or 50M Total reads. Standardized gene set enrichment methodology was used to compare changes in specific gene sets over time in each treatment group. Data were analyzed using heat maps, enrichment plots, and dot plots for individual genes. Leading edge genes were examined in relevant pathways and in relationship to phenotypic changes on liver biopsy, including fibrosis stage.

Results from these studies are summarized below:

Cell Metabolism

Oxidative phosphorylation upregulated by treatment with tesamorelin;

Leading edge genes correspond to genes that encode primarily:

Components of electron transport chain;

Chaperone proteins needed to assemble electron transport chain;

Enhanced mitochondrial activity may reduce reactive oxygen species (ROS) levels, preventing inflammation and fibrosis in the liver.

Inflammation

Tesamorelin leads to a robust downregulation of multiple inflammatory pathways. (e.g., TNF-alpha, IL-6 and IL-2);

Inflammation is an important process in NAFLD progression (e.g., NASH);

Gene analysis appears to be more sensitive to detect changes in inflammation that were not reflected overtly in histopathology analyses;

Leading edge genes correspond to genes that encode primarily:
Components of innate and adaptive immune cells;
Cytokines.

Tissue Repair

Tesamorelin led to a downregulation of genes involved in tissue repair;

Fibrosis is a manifestation of a chronic/dysregulated wound healing response. Notably, among tesamorelin-treated participants, it was found that downregulation of gene pathways involved in tissue repair corresponded to a reduction in genes associated with fibrosis stage;

Apoptosis genes downregulated in tesamorelin-treated participants;

UV response genes downregulated in tesamorelin-treated participants;

Epithelial to mesenchymal transition (EMT) genes downregulated in tesamorelin-treated participants;

Transforming growth factor-beta (TGF-β), a key mediator of fibrosis, EMT, and tumorigenesis, was downregulated in tesamorelin-treated participants.

Cell Turnover

Tesamorelin led to a downregulation of genes involved in cell turnover;

Earliest event in NAFLD, even prior to steatosis, has been shown to be liver proliferation; has been posited as an important step in liver damage;

Repetitive cycles of apoptosis and proliferation of hepatocytes increase the risks of aberrant repair in some individuals, culminating in tumor initiation.

Cancer Prognosis Gene Sets

Tesamorelin led to upregulation of HCC good prognosis and downregulation of HCC poor prognosis gene sets; downregulation of Yap Taz pathway gene set, involved in fibrosis and oncogenesis;

Consistent with its downregulation of inflammation, fibrogenic, and cell turnover pathways, which together may culminate to reduce malignancy risk Tesamorelin appears to decrease hepatic malignancy potential, even while agonizing the GH pathway and increasing systemic IGF-1 pathways Relationship of Specific Pathways to Changes in Fibrosis Genes (within Tesamorelin Group)

The gene set involved with oxidative phosphorylation negatively related to change in fibrosis genes;

The gene sets involved in inflammation, tissue repair, cell turner positively related to change in fibrosis genes.

Although the present disclosure has been described hereinabove by way of specific embodiments thereof, it can be modified, without departing from the spirit and nature of the subject disclosure as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for (i) preventing or delaying the onset of liver fibrosis or (ii) reducing liver fibrosis or the progression thereof, in a subject suffering from nonalcoholic fatty liver (NAFL) or nonalcoholic steatohepatitis (NASH), wherein said subject has a hepatic fat fraction (HFF) of at least about 10%, comprising administering an effective amount of trans-3-hexenoyl-GHRH$_{(1-44)}$-NH$_2$ or a pharmaceutically acceptable salt thereof to said subject.

2. The method of claim 1, wherein said subject has a hepatic fat fraction (HFF) of at least about 15%.

3. The method of claim 1, wherein said subject has a hepatic fat fraction (HFF) of at least about 20%.

4. The method of claim 1, wherein said subject has serum ALT levels of at least about 30 U/L.

5. The method of claim 1, wherein said subject has serum ALT levels of at least about 35 U/L.

6. The method of claim 1, wherein said subject has a NAFLD Activity Score (NAS) of at least 1 as measured by the NAS Clinical Research Network (NAS CRN) scoring system.

7. The method of claim 1, wherein said subject has a NAFLD Activity Score (NAS) of at least 2 as measured by the NAS Clinical Research Network (NAS CRN) scoring system.

8. The method of claim 1, wherein said subject has a NAFLD Activity Score (NAS) of at least 3 as measured by the NAS Clinical Research Network (NAS CRN) scoring system.

9. The method of claim 1, wherein said subject has a NAFLD Activity Score (NAS) of at least 4 as measured by the NAS Clinical Research Network (NAS CRN) scoring system.

10. The method of claim 1, wherein said subject has a reduction of hepatic fat fraction (HFF) by at least 4% (absolute reduction) following the treatment.

11. The method of claim 1, wherein said subject has liver fibrosis.

12. The method of claim 11, wherein said subject has a fibrosis score of at least 1C prior to the treatment.

13. The method of claim 11, wherein said subject has a fibrosis score of at least 2 prior to the treatment.

14. The method of claim 1, wherein said subject suffers from human immunodeficiency virus (HIV) infection.

15. The method claim 1, wherein said subject has a body mass index (BMI) of at least about 25.

16. The method of claim 1, wherein said pharmaceutically acceptable salt of trans-3-hexenoyl-$GHRH_{(1-44)}$-$NH_2$ is an acetate salt.

17. The method of claim 1, wherein said trans-3-hexenoyl-$GHRH_{(1-44)}$-$NH_2$ or pharmaceutically acceptable salt thereof is administered by subcutaneous injection.

18. The method of claim 1, wherein said trans-3-hexenoyl-$GHRH_{(1-44)}$-$NH_2$ or pharmaceutically acceptable salt thereof is present in a pharmaceutical composition comprising at least one pharmaceutically acceptable excipient.

19. The method of claim 18, wherein said trans-3-hexenoyl-$GHRH_{(1-44)}$-$NH_2$ or pharmaceutically acceptable salt thereof is present in said pharmaceutical composition at a dose of about 1 mg/ml to about 10 mg/ml.

20. The method of claim 18, wherein said trans-3-hexenoyl-$GHRH_{(1-44)}$-$NH_2$ or pharmaceutically acceptable salt thereof is present in said pharmaceutical composition at a dose of about 1 mg/ml to about 8 mg/ml.

21. The method of claim 18, wherein said trans-3-hexenoyl-$GHRH_{(1-44)}$-$NH_2$ or pharmaceutically acceptable salt thereof is present in said pharmaceutical composition at a dose of about 4 mg/ml to about 8 mg/ml.

22. The method of claim 1, wherein said trans-3-hexenoyl-$GHRH_{(1-44)}$-$NH_2$ or pharmaceutically acceptable salt thereof is administered at a daily dose of about 1 mg to about 2 mg.

* * * * *